US011766028B2

(12) United States Patent
Sarzen et al.

(10) Patent No.: US 11,766,028 B2
(45) Date of Patent: Sep. 26, 2023

(54) METHODS AND SYSTEMS FOR USING SOUND DATA TO ANALYZE HEALTH CONDITION AND WELFARE STATES IN COLLECTIONS OF FARM ANIMALS

(71) Applicant: AgLogica Holdings, Inc., Peachtree Corners, GA (US)

(72) Inventors: Marcel Joseph Sarzen, Sandy Springs, GA (US); Joseph Marcel Sarzen, Sandy Springs, GA (US); Christopher G. Rosati, Duluth, GA (US)

(73) Assignee: Aglogica Holdings Inc, Peachtree Corners, GA (US)

( * ) Notice: Subject to any disclaimer, the term of this patent is extended or adjusted under 35 U.S.C. 154(b) by 0 days.

(21) Appl. No.: 16/891,744

(22) Filed: Jun. 3, 2020

(65) Prior Publication Data

US 2021/0298272 A1 Sep. 30, 2021

Related U.S. Application Data

(60) Provisional application No. 62/856,881, filed on Jun. 4, 2019.

(51) Int. Cl.
*A01K 29/00* (2006.01)
*G10L 25/66* (2013.01)
(Continued)

(52) U.S. Cl.
CPC .............. *A01K 29/005* (2013.01); *A61B 5/48* (2013.01); *A61B 5/742* (2013.01); *G05B 19/406* (2013.01);
(Continued)

(58) Field of Classification Search
CPC ................................ A61B 7/04; A01K 29/005
See application file for complete search history.

(56) References Cited

U.S. PATENT DOCUMENTS 8,838,260 B2  9/2014 Pachet et al.
8,915,215 B1  12/2014 Helgeson
(Continued)

FOREIGN PATENT DOCUMENTS

KR  1018946350000  9/2018
WO  2018/091383  5/2018

OTHER PUBLICATIONS

Longshen, L., Li, B., Zhao, R., Yao, W., Shen, M., & Yang, J. (Jan. 13, 2020). A Novel Method for Broiler Abnormal Sound Detection Using WMFCC and HMM. Retrieved from https://www.hindawi.com/journals/js/2020/2985478/.
(Continued)

*Primary Examiner* — Fabricio R Murillo Garcia

(57) ABSTRACT

Systems and methods are described for selecting a sound type of interest from a first (e.g., master/global) machine learning library comprising information derived from reference audio stream data acquired from a plurality of farm animal operation reference sound monitoring events, including from a first farm animal operation monitoring event of a first farm animal operation, wherein the sound type of interest is associated with a condition state of interest of a first collection of farm animals. Further, information associated with the selected sound type of interest can be included a second machine learning library, wherein the second machine learning library is operational on an edge computing device located in proximity to a second farm animal operation. Audio stream data can be acquired from the second farm animal operation in a second farm animal operation monitoring event, and processed using the second machine learning library information to determine whether the sound type of interest is present in the acquired audio stream data, thereby generating information associated with
(Continued)

the presence or absence of the condition during the second farm animal operation monitoring event.

20 Claims, 13 Drawing Sheets

(51) Int. Cl.
*G06N 20/00* (2019.01)
*G06N 5/04* (2023.01)
*A61B 5/00* (2006.01)
*G05B 19/406* (2006.01)
*H04L 67/12* (2022.01)
*H04R 1/40* (2006.01)
*H04R 3/00* (2006.01)
*H04L 67/10* (2022.01)

(52) U.S. Cl.
CPC ............... *G06N 5/04* (2013.01); *G06N 20/00* (2019.01); *G10L 25/66* (2013.01); *A61B 2503/40* (2013.01); *G05B 2219/45113* (2013.01); *H04L 67/10* (2013.01); *H04L 67/12* (2013.01); *H04R 1/406* (2013.01); *H04R 3/005* (2013.01)

(56) References Cited

U.S. PATENT DOCUMENTS

| | | | |
|---|---|---|---|
| 9,786,146 B2 | 10/2017 | Markwell et al. | |
| 9,899,034 B2 | 2/2018 | Hofer et al. | |
| 10,362,769 B1 | 7/2019 | Kartoun et al. | |
| 2008/0059264 A1* | 3/2008 | Stroman | G06Q 10/063 705/7.32 |
| 2013/0150744 A1* | 6/2013 | Brattain | G16H 50/30 600/529 |
| 2015/0282457 A1* | 10/2015 | Yarden | A61D 17/002 340/573.2 |
| 2019/0250882 A1* | 8/2019 | Swansey | G06F 3/167 |
| 2019/0297855 A1* | 10/2019 | Wolf, II | A01K 31/20 |
| 2020/0065966 A1* | 2/2020 | Spencer | G06T 7/11 |

OTHER PUBLICATIONS

Curtin, Ryan & Daley, Wayne & Anderson, David. (2015). Classifying broiler chicken condition using audio data. 2014 IEEE Global Conference on Signal and Information Processing, GlobalSIP 2014. 1141-1144. 10.1109/GlobalSIP.2014.7032300.

* cited by examiner

Production Cycle: Sound Data Application Examples

- Poultry Production
    - Breeders
    - Layers
    - Hatchery
    - Broilers
        - Grow Cycle: 6-8 weeks (chicks to mature birds)
    - Important Metrics
        - Animal Vocalization: Respiratory disease, Stress, Daytime activity profiling, Nighttime activity profiling
        - Production Operations: Feed Delivery, Water availability, Ventilation, Heating System
    - Turkeys
        - Grow Cycle: Brooding - temp control (5-6 weeks), growing (5-6 weeks)
- Swine Production
    - Estrus/Gestation
    - Farrowing (3 weeks)
    - Nursery (6-8 weeks)
    - Growing and Finishing (16-17 weeks)
    - Important Metrics
        - Animal Vocalization: Coughing, Respiratory disease, Stress, Daytime activity profiling, Nighttime activity profiling
        - Production Operations: Feed Delivery, Water availability, Ventilation, Heating System

FIG. 4

METHODS AND SYSTEMS FOR USING SOUND DATA TO ANALYZE HEALTH CONDITION AND WELFARE STATES IN COLLECTIONS OF FARM ANIMALS

CROSS-REFERENCE TO RELATED APPLICATION

This application claims priority to U.S. Provisional Application No. 62/856,881 titled "METHODS AND SYSTEMS FOR USING SOUND DATA TO ANALYZE HEALTH CONDITION STATES IN COLLECTIONS OF LIVESTOCK ANIMALS," filed Jun. 4, 2019, which disclosure is incorporated herein in its entirety.

FIELD OF THE DISCLOSURE

This application relates to farm animal monitoring, and more specifically, detecting a condition state of interest in farm animals.

BACKGROUND OF THE DISCLOSURE

Modern commercial production facilities, also termed "farm animal operations" herein, are businesses. This means that farm animal operators must maintain consistent supply chains that can ensure that customers—be they groceries, restaurants, or commercial facilities—will obtain a meat product on an as-needed basis. In other words, the supply chain must be managed and maintained to ensure that the customer receives the meat product as needed, while keeping the supply restricted enough to maintain the profit margins needed to sustain the business. The condition states under which animals are raised for meat production must therefore be closely controlled to ensure that farm animal maturation is substantially uniform for the intended business use of a particular type of farm animals, and that there is substantially no break in the supply chain. It follows that considerable efforts must be made to reduce the uncertainties imparted by the variables used by the biological characteristics of the animals from which the meat products are generated.

Given the industrial nature of modern farm animal operations, growing processes are optimized not only for the specific animal type, but also for the particular lifecycle stage of the animal. For example, in the production of poultry for consumption, also called "broilers," the process is very much an industrial one. There are 8 distinct aspects of a modern poultry processing supply chain: 1) primary breeders, 2) feed mill, 3) breeders, 4) hatchery, 5) grow-out farms/houses, 6) processing plants, 7) further processing, and 8) transportation and marketing. Of these, the first 5 are integrally entwined with the fact that live animals are involved and, as such, each of these steps can be greatly influenced by biological issues that can arise in living systems. Given the high density of animals that can be present in a single farm animal operation location, problems such as infections can spread quickly. This makes illness that interrupts the farm animals supply chain a significant threat to the economic success of operators, especially given the low margins that often are present in farm animal operations.

Moreover, it has been estimated that today farm animal operators achieve less than 80% of the genetic potential of their flocks, which means that cost-effective improvements could allow them to enhance their outputs, even assuming that the best genetic stock is present at the start. This would not only help farmers to make more profit per unit of animal but could also allow more protein to be generated to be obtained with fewer animals. Efficiencies in protein delivery would have the attendant benefit of reducing waste and pollution caused by farm animal operations, among other things.

To reduce potential variability in poultry production processes, standards have been established in modern facilities. Grow house temperature, humidity, and lighting are automatically controlled. Feeding, watering and even vaccination and medication are increasingly delivered automatically. Such precise control of the operational aspects of a commercial farm animal facility is desirable so that a number of animals are present in an appropriate lifecycle stage at a particular time. That is, a farm animal operation can be imagined as akin to a production facility where inputs are generated as a function of outputs to be delivered to a customer on an expected schedule and in a contracted amount.

Chickens take only six weeks to go from hatching to finished weight; stressful condition states can retard their growth, reducing their value when they go to market. Deviation from any of the growth parameters in these live chickens can result in their being ready for processing earlier or later than expected and/or not being of a quality or character expected. Failure of a flock to grow and thrive as expected for a production process can significantly affect the amount paid for a particular farm animal harvesting event, especially since the finances of most farm animal operations today are highly aligned with obligations that require a farmer to comply with contracted outcomes that are defined well-before a farm animals lifecycle begins. Thus, close control of condition states at each stage of a poultry processing operation is desired to better ensure that the outcome of a poultry lifecycle process is consistent.

The ability to detect illnesses occurring in a flock is highly desirable in modern poultry production facilities. Due to the large number of chickens in the flock morbidity (i.e., illness) is usually only noticed once a large portion of the flock shows significant symptoms of a certain disease, or once mortality rate is high enough to be noticed. By that time, up to 100% of the flock could be infected, and treatment required can be massive. Alternatively, the whole flock may need to be destroyed or an infected flock may need to be diverted to lower value uses, such as for pet food, as opposed to being sold for human consumption.

The continued alignment of health condition states with production standards can be better ensured by having experienced farm staff closely monitor a flock during their lifecycles. Poultry farmers have long contended anecdotally that the sounds that a flock makes can provide insights into the relative contentedness of the birds in the flock, and such subjective information is known by farmers to be directly related to the health and well-being of the flock. From a poultry professional's viewpoint, such flock "contentedness" is thought to be indicative, at least in part, to the financial success of a particular growth cycle. However, human presence inside the chicken house today is deliberately kept at minimum and human inspection of the flock's productivity and health can be less frequent than needed to maintain optimum knowledge about the flock condition in real time. The reasons for such limited human involvement are several: increased labor costs, labor shortages, biosecurity concerns, among others. As a result, in person visual inspections of flocks are typically carried out from time to time by a trained farm animal supervisor/manager who works for a company that owns the farm animal output from a farmer, and are carried out even less frequently by a veterinarian. Moreover, the increased automation of farm animal operations means that it has become less likely that humans will be present in a poultry grow out operation, even while knowledge of disease states currently requires experts to gauge the health of the flocks while onsite.

Time is of the essence in farm animal operations. As noted, time from hatching to harvest is short, and each life stage is precisely measured. To maintain the health of their flocks so as to meet production goals, farm animal operators attempt to act quickly when an illness is suspected in a collection of farm animals. Farm animal operators and other animal producers therefore sometimes resort to widespread use (via injections or mixing with feed) of antibiotics and other medications in an attempt to prevent infections and reduce the occurrence of pathogens within their animals, often using existing automated dispensing processes. However, many of the same or similar pathogens that infect farm animals can also infect humans, and there is increasing concern in the human medical community that such widespread use of antibiotics, which frequently are the same as used in treatment of human illnesses, is leading to resistance buildup in the targeted pathogens and in other pathogens. When these resistant pathogens are transmitted to humans via the animal products and by other means, the result can be a general loss of effectiveness of these antibiotics in the treatment of humans.

The desire to reduce antibiotics, hormones, etc., in the production of farm animals has generated a desire for operators to more closely monitor farm animal operations to better ensure that respiratory or other illnesses that can be observable can be detected before they spread beyond a small group of animals. As would be appreciated, the decreased ability to prophylactically dispense antibiotics and hormones to flocks has made it harder to ensure a healthy and robust bird for harvest. Unfortunately, this desire for closer monitoring of farm animal operations for early stage occurrence of illness that could infect an entire collection of farm animals has occurred at the same time labor shortages have arisen throughout the farm animal production industry, even while profit margins have continued to decline for farmers and the overall movement toward automation has increased.

While other forms of farm animal production facilities are generally populated by a fewer number of animals per location and harvesting operation than in poultry production, such facilities have also been increasingly standardized with tight controls put on the operations as industrialized meat production has become the norm. The value of each individual animal to the overall success of the operation is also more than with an individual chicken in a poultry operation, even while the lifecycle of a dairy cow/cattle or pig is much longer. Thus, stakeholders in these types of farm animal operations are also highly concerned with maintaining the health of their animals at all stages of the production processes. The supply chain must be maintained in these operations.

To this end, pig vocalizations can be a sign of stress (or the lack thereof) in an environment. Respiratory problems are very common in pig herds, causing significant economic losses. Early treatment of problems can be crucial for reducing the economic losses and the amount of antibiotics used to curtail illness in an affected pig. Early warnings for the problem can allow for earlier treatment, causing fewer animals to be infected, taking less time to cure the animals, and therefore minimizing the animal performance impact due to the morbidity event.

Consumers are also increasingly seeking meat sources that are associated with "humane" growth and processing operations. To this end, a farm animal operation can become "Certified Humane" by complying with a large number of requirements that require monitoring and documentation. These requirements include close monitoring of the environmental condition states in which the farm animals are raised, more space for the farm animals, and visual review of the farm animals on a regular basis to assess the health condition of the animals. Even while consumers are increasingly demanding farm animal operators to provide them with meat for consumption that require more effort for farmers and additional labor costs, consumers are not necessarily willing to pay more for a more expensive-to-produce product. All aspects of the animals' lifecycle, from hatching/birth to the consumer must be trackable for the necessary humane certification, including whether the animal experienced any unnecessary pain or discomfort during its life. This includes animal welfare monitoring as the animals are being unloaded and prepared for meat processing.

There remains a desire for improvements in the monitoring, detection, prediction, treatment, etc. of farm animal collection health and other relevant farm animal collection condition states during the lifecycles thereof and the evaluation of new animal health and nutrition solutions. The present disclosure provides this and other benefits.

BRIEF DESCRIPTION OF THE DRAWINGS

FIG. 4 illustrates example sound data application examples, in accordance with example embodiments of the present application.

DETAILED DESCRIPTION OF THE DISCLOSURE

Figure 1:
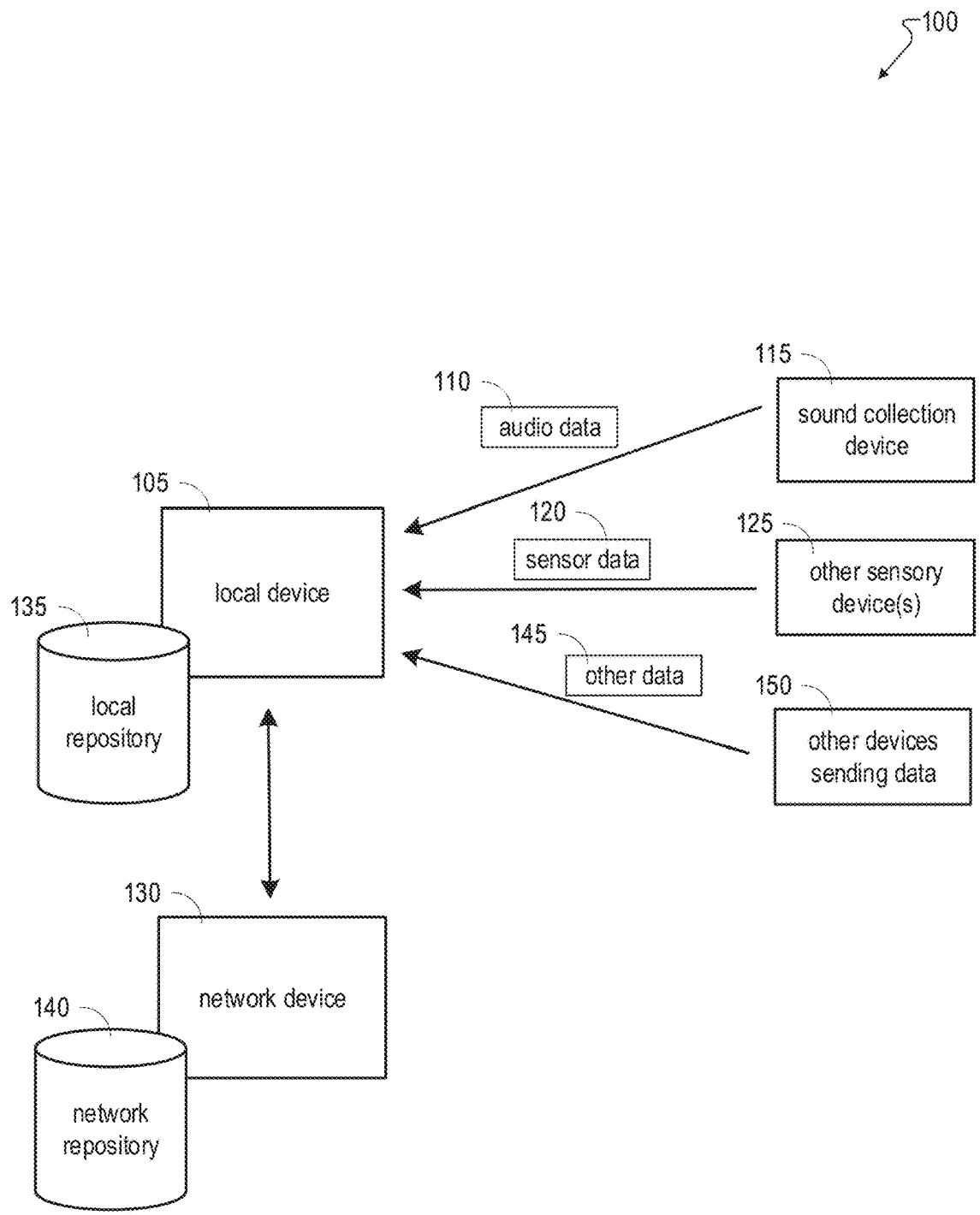
FIG. 1 shows an example of a farm animal operation monitoring system and some components used in the system, such as an edge computing device (local device), also a networked device (e.g., a cloud server), and various sensors, in accordance with example embodiments of the present application.

In the following detailed description, reference is made to the accompanying drawings, which form a part hereof, and within which are shown by way of illustration certain embodiments (also referred to herein as implementations) by which the subject matter of this disclosure may be practiced. It is to be understood that both the foregoing general description and the following detailed description are exemplary and explanatory only and are not restrictive of the disclosure, as claimed. It is to be understood that other embodiments may be utilized and structural changes may be made without departing from the scope of the disclosure. In other words, illustrative embodiments and aspects are described below, including in the form of structures and devices shown in block diagram form. For example, the methods (e.g., processes, functions, and logic flows) described in this specification can be performed by devices (e.g., server, computer, etc.) comprising programmable processors that execute machine executable instructions to facilitate performance of the operations described herein. Examples of such devices can be devices comprising circuitry and components as described in FIG. 13.

But it will of course be appreciated that in the development of any such actual embodiment, numerous implementation-specific decisions can be made to achieve specific goals, such as compliance with system-related and business-related constraints, which may vary from one implementation to another. Moreover, it will be appreciated that such development effort might be complex and time-consuming but would nevertheless be a routine undertaking for those of ordinary skill in the art having the benefit of this disclosure.

Unless defined otherwise, all technical and scientific terms used herein have the same meaning as is commonly understood by one of ordinary skill in the art to which this disclosure belongs. In the event that there is a plurality of definitions for a term herein, those in this section prevail unless stated otherwise.

As used herein, a "collection" can comprise at least one, or a plurality of the subject farm animals. As would be appreciated, a "collection" of a particular animal type would typically have meaning in context. For example, a collection of farm animals that comprise chickens is often termed a "flock," In such usage, a flock will represent a group, or "collection," of poultry farm animals that are of approximately the same age (e.g., were hatched at approximately the same time) and, as such, are of approximately the same lifecycle stage at a particular time. In poultry production scenarios, a "collection" can comprise thousands, or tens of thousands of animals that can be present at a lifecycle stage that is approximately equal for all of a single collection of chickens. In a different context, a "collection," of pigs can be a plurality of pigs that are present as a group in a farming operation, such as those pigs that will share a building where they will eat, sleep, exercise, etc. together with the intention that they be harvested together or otherwise utilized in a similar way, such as for milk production for cows, etc. Typically, a collection of pigs, dairy cows, cattle, etc. will generally be of approximately the same age, size, etc. since modern farm operations often dictate the grouping of animals having similar characteristics and lifecycle stage for processing efficiency. However, in some implementations, a "collection" of farm animals can comprise individual animals of different ages, such as in a situation where a juvenile animal is in the presence of its mother while nursing or the like.

A "farm animal operation" where the farm animal sound is acquired for review for farm animal condition state will be understood in context. For example, a farm animal operation can be a hatchery, a grow out house, laying house, etc. if the farm animal is a chicken. If the farm animal is a pig, the "farm animal operation" can be a farrowing barn, a nursery barn, a finisher barn, a gestation barn, or any location where the animal is kept prior to slaughter. If the farm animal is cattle, the "farm animal operation" can be a feedlot or any location where the animal is kept prior to slaughter. If the farm animal is a dairy cow, the "farm animal operation" can comprise a grazing area, barn, or the like. Other examples are appropriate in context for an animal type, as well as the lifecycle of the farm animals.

In broad constructs, the disclosure relates to devices, systems, and methods of conducting real time or near real time monitoring of one or a plurality of farm animal operations of interest of an acquired farm animal operation audio stream. In some implementations, sound type information associated with other relevant farm animal operation information, such as environmental information (e.g., temperature, humidity, background noise, lighting characteristics, feed/water/medicine amounts, etc.) that might be relevant to the subject operation can also be analyzed. Monitoring can also be via retrospective analysis of the acquired audio stream and associated information in some implementations.

The processes can occur in one or more farm animal operation monitoring events in which farm animal collection audio feeds and, in some cases, additional information is obtained from a farm animal operation. The farm animal operation sound data and associated information can be acquired from locations proximate to a collection of farm animals of interest for monitoring for one or more conditions of interest. The monitoring of the acquired farm animal operation audio stream and associated information can be via the analysis of the acquired data for the presence or absence of a farm animal operation sound of interest with or without the presence or absence of other information, such as environmental conditions associated therewith. The farm animal operation sound of interest can be associated with one or more animals in a farm animal collection, where the sound of interest can be associated with a health or welfare condition of interest for one or more farm animals present in the subject farm animal collection.

For analysis of an acquired farm animal operation audio stream, reference farm operation sound data information can be acquired from a plurality of reference sound data monitoring events, and such acquired sound configured for use in as reference farm operation sound data (which can also be referred to as a sound database). The reference farm operation sound data are suitable for use in machine learning processes that are at least partially, and in some implementations, are fully operational on a device that is located on or proximate to the farm animal operation that is being monitored in a monitoring event. The information in the farm animal operation reference sound data is associated with data elements (e.g., has been tagged or labelled) that are relevant to the farm operations of interest, and at least some of the tagged and labelled sound data has been validated prior to use in the reference farm animal operation sound library, as discussed further herein. Such farm animal operation sound type monitoring and analysis can be conducted substantially on onsite of the farm operation of interest in real time using the edge computing methodology herein.

In a non-limiting example, a farm animal collection can comprise a poultry flock present in a grow-out house, for example, chicken or turkey farm animal operations. As would be appreciated, grow-out houses are specialized buildings that allow age appropriate control of temperature, humidity, food delivery, water delivery, and lighting for broilers. The grow-out house is typically completely enclosed to prevent predator entry and to promote biosecurity. The health condition state desirable of detection in a collection of such farm animals can comprise one or more respiratory infections. A number of poultry-related respiratory ailments (e.g., infectious bronchitis, Avian pneumovirus, Lentogenic Newcastle disease, virus, vaccinal and other strains) may be present in one or a plurality of chickens in a collection of chickens, that is, a flock, that is being raised for harvest in a production setting such as grow out house. Audible signs of such infections in the chickens during their time in a grow-out house can be snicking/sneezing or rale (e.g., a gurgling or rattling noise). Morbidity as a result of such respiratory illnesses is can be 10-20%, or less or more, for poultry; as such, early detection of these illnesses is highly desirable, at least because reduction in the number of dead or condemned (e.g., euthanized) birds can exceed 5 or 10% of an infected flock. Notably, because flocks can comprise 10K or even many more animals in a single collection, it can be exceedingly hard to visually detect a small number of ill or potentially ill animals through visual observation of individual animals.

In another implementation, a health condition state of pigs, dairy cows, cattle, etc. can be discerned from reference farm animal operation sound data appropriately generated for these specific animal types and the various lifecycles and events associated with such animals. To this end, pig coughs can be monitored using reference farm animal operation sound data acquired from a comparable collection of pigs where such sound is evaluated and labeled for use in machine learning processes as discussed elsewhere herein. Dairy cows and cattle can also be monitored for sounds of illness or symptoms of illness, such as coughing, sneezing, or the like.

With respect to the edge computing methodology that forms an aspect of the present disclosure, substantial benefits can be provided over methodologies that require sound processing and analysis to take place at an offsite location, such as on a cloud computing server or the like. In a substantial benefit, notification of the presence or absence of a farm operation sound type of interest in a farm animal operation acquired audio feed can be provided by a device that is located at or near the point where the audio feed is generated, that is, on the subject farm operation premises or proximate thereto. The ability to detect the farm animal operation sound type(s) of interest, as well as other information relevant thereto, on location can thus have the generation of the desired information to not be dependent on the availability of a robust and continuous network connection to a cloud server or other communications methodology, such as Wi-Fi or cellular connection, to perform the farm animal operation sound type analysis methodology herein. Such on-premises operation can be beneficial in farm animal operations which are often present in rural locations where Wi-Fi and cellular signal communications may be limited, intermittent, or even non-existent.

FIG. 1 describes an example implementation of a farm animal operation monitoring system(s), e.g., farm animal operation monitoring system 100 that can perform the functions, operations, and methods described in the present application. In accordance with the farm animal operation monitoring improvements herein, sound processing and analysis capability can be substantially resident on a local device (e.g., sound processing and analysis device) 105 present at the location of the farm animal operation. While labeled "sound processing and analysis device" for convenience, this label of this device is non-limiting, and it is intended that any computing device having the appropriate computer-executable modules to perform the functions, methods, and operations described in this disclosure, or implement the features as described in this disclosure, can suffice.

The farm animal operation monitoring system 100 (e.g., which can comprise local device 105) of the present disclosure can be configurable to process audio data 110 (also referred to herein as sound data) based on sound acquired from a sound collection device 115, including high density audio data. In example implementations, sound processing and analysis can be performed by the local device 105, which can be an edge computing device, wherein edge computing uses a distributed computing architecture that brings computation and data storage closer to the location where it is needed (e.g., "edge" of the network), to improve response times and save bandwidth. Moreover, many livestock animal operations are located in rural areas, where cellular or internet access might be very limited, or non-existent due to lack of communication infrastructure. The audio data can be collected during a farm animal monitoring event (e.g., audio data obtained from a first farm animal monitoring event). Other types of sensor data 120 (e.g., video data, thermal data, environmental data) can also be collected, e.g., by other sensory device(s) 125, and associated with the audio data 110. The farm animal operation monitoring system 100 can also be configured to identify the sound type(s) of interest therefrom, as well as other relevant data associated therewith. This processing and identifying, in example implementations, can be substantially performed without having to upload the subject data streams to a separate device (e.g., a network device 130, which can be a network server or a cloud server device). Relevant sound libraries and associated information can be operational on machine learning processes substantially resident on an on-location device. To this end, this edge computing capability configured in the farm animal operation monitoring systems of the present disclosure incorporates robust and yet still modular and flexible artificial intelligence (AI) modules and machine learning (ML) modules having AI and ML capability. For example, when the farm animal operation sound libraries and other associated information that is operational to identify the sound type(s) of interest and other relevant information in a farm animal operation audio stream are configured with one or more farm animal operation sound types of interest for a particular use case, such sound types and associated information are each, independently, associated with classifiers, feature sets, processing instructions, etc. relevant thereto.

The subject machine learning libraries can be generated in a cloud computing environment, with the relevant aspects of the libraries selectable or derivable therefrom to enable a lighter weight machine learning library to be operational in or proximate to the farm animal operation of interest. For example, a machine learning library operational in a cloud computing environment can include sound data for all life stages of a livestock animal that is a chicken, but an edge computing device operational in a grow out house can incorporate only sound data that is relevant to the grow out stage. Moreover, when the relevant farm animal operation sound libraries and associated information libraries are enhanced, modified or corrected, the changes can be communicated to the farm animal operation monitoring systems from the cloud computing environment. When the farm animal operation sound type library and/or additional information is changed on a monitoring system operational in a specific locations, such changes can be transmitted to the more comprehensive farm animal operation sound libraries and other information libraries resident in a cloud computing environment for distribution as appropriate to other farm animal operation monitoring systems operational in other environments. The sound libraries, associated information, and other relevant information can be stored in a local repository 135 associated with a local device 105, which can be placed locally or on the edge, or can be stored in a networked repository 140 associated with a network device 130. Other data 145 (e.g., weather or environmental data, farm animal genetic and source information, food or feed data, production operation parameters, mortality data, medicines administered, etc.), as described further below, including with respect to FIG. 3, FIG. 4, and FIG. 5, can also be processed and considered by the farm animal operation monitoring system(s) 100, including in example implementations, by a network device (e.g., cloud device, network server, etc.).

In an example implementation, the farm animal operation audio stream (e.g., audio data 110) that is desired to be monitored at a location of interest—that is the farm animal operation audio stream that comprises sound generated from a collection of farm animals present at a farm animal operation of interest and any areas proximate thereto—can be automatically segregated into individual audio tracks on the device by audio processing capabilities resident thereon. For example, a high pass filter can be applied to the farm animal operation audio stream prior to processing of the audio for sound content. As would be appreciated, such segregation of different farm animal operation sound sources into separate audio tracks can enable the detection of a farm animal location sound type of interest from a generated farm animal operation audio stream that can include a plurality of sound types therein. However, such audio track segregation can be obviated if the system is configurable to identify a farm animal operation sound type of interest from the entirety of the farm animal operation audio stream that can comprise two or more sounds types having different sources or origins.

The farm animal operation monitoring system(s) 100 of the present disclosure can comprise hardware configured for edge computing, as would be appreciated by one familiar with IoT ("Internet of Things") devices. Such processing capabilities can be provided, for example, by a Raspberry Pi processor that is configured to be in communications engagement with a sensor having farm animal operation audio stream acquisition capability. The Nvidia Jetson® series of processors can also suitably be used as local device 105. Farm animal operation audio stream acquisition capability can be provided by a sound collection device 115, for example a microphone configured in a single device packaged with the edge computing processor and other componentry, such as with a microphone that is configured with the processor in a standalone device. Yet further, one or a plurality of wireless microphones configured at various locations in and proximate to the farm animal operation of interest can be in communications engagement (e.g., connected by WIFI, Bluetooth, or RFID) with the audio stream collection and analysis device, as long as the configuration of the microphone(s) as a separate component that is in communications engagement with the processor that operates substantially without undue latency. The use of a plurality of wireless microphones that are in communications engagement with the edge computing processor can facilitate the generation of a farm animal operation audio stream that is collected at different vantage points in a single farm animal operation location, such as in a large room in which a plurality of farm animals are resident. The device (e.g., local device 105) used to collect, process, and/or analyze the farm animal operation audio stream can comprise other relevant electronics features, such as amplifiers, sound generation capabilities (e.g., lights or alarms).

Other sensory device(s) 125 can comprise sensors that are capable of tracking movement or tracking individual animals, groups or densities of farm animals of interest, other animals (e.g., predators, etc.), humans, or moving objects can also be configurable with the farm animal operation monitoring processes herein. Still further, other types of useful information can be derived from other sensory device(s) 125, such as to obtain thermal data via infrared sensors. Yet other sensory device(s) 125 can comprise environmental sensors associated with the farm animal operation monitoring systems that generate additional information that can be relevant to the conditions present in the location or business. Such collection of environmental information (humidity, temperature, carbon dioxide, carbon monoxide etc.) can provide further context to the information derivable from the farm animal operation audio stream. Information derivable from the interaction of the farm animal operation audio stream and data obtainable from other associated sensors can be used to enrich the information obtainable from the farm animal operation sound monitor systems. To this end, the associated information can be incorporated in the farm animal operation sound libraries for use in machine learning processes from which useful information about one or more farm animal operations. The additional information can be validated by a person using a user equipment (UE), and/or a computer, or updated from time to time. UE can comprise a desktop computer, laptop computer, tablet, smartphone, smartwatch, or the like. The additional information can also be removed from the information associated with the sound libraries.

The local device 105, which as mentioned above can be an edge computing device, that is operational in farm animal operation monitoring system(s) 100 can also comprise a power source. In some implementations, the local devices operational with the monitoring systems can be connected to a power source, such as via connection to an electrical power outlet, USB power source, or external battery. When connected to a power source, the devices can incorporate a battery backup. In other implementations, the power source for the device(s) can be a rechargeable battery, such as a lithium ion battery. It would be appreciated that the real-time or near real-time audio stream monitoring functionality typically would require that the device(s) be connected to power at all times that the device(s) are intended to capture and process a farm animal operation audio stream. As such, the devices can be configured to provide a notification or alert when the battery power is removed from the power source, the battery is depleted, or the device(s) is otherwise non-operational.

When the local device(s) 105 comprise battery powered device(s) or are associated with battery powered device(s), the componentry can be characterized as "low power," in order to extend the time that the device(s) can be operational without substantial reliance on replacement or recharging of a battery.

In some implementations, methods to reduce the computational complexity involved with acquiring, analyzing, and, if appropriate, providing notifications associated with the farm animal operation sound type of interest and other pertinent information can be used. Notably, because the farm animal operation sound types of interest and associated information for identification from a locational farm animal operation audio stream will, by definition, be those that may be relevant in context to the user, manager, supervisor, or owner of the farm animal operation from which the farm animal operation audio stream and other information is being acquired and analyzed, the scope of the sound type and other information libraries can also be streamlined. The sound type and other information libraries that are operational in the farm animal operation monitoring system can thus be "fine-tuned" to allow the farm animal operation sound type and other information identification to focus on one or a set of use cases relevant to the farm animal operation of interest in a particular location or having particular characteristics.

The selectability of farm animal operation sound types of interest for operation in a specific farm animal operation monitoring event, as well as other pertinent information, in a particular situation from the library of farm animal operation data can facilitate the operation of the machine learning processes in the edge computing environment (e.g., local device 105 can be an edge computing device) at least because the sound data type libraries and associated information can be selected specifically to address the information relevant to a particular farm animal operation location. This can result in a "lighter," more efficient, and streamlined operation of machine learning processes that can be operational on the edge computing devices herein. In other words, the machine learning processes operational on each farm animal operation monitoring device at a particular location or type of location can include only those farm animal operation sound types library data categories and other specific information that may be relevant thereto. For example, sound type information that is relevant to a turkey flock in a grow out operation and environmental information (e.g., temperature, humidity, etc.) that is relevant to the time of year that the farm animal operation is being monitored can be derived from a master sound data library and only those aspects of the farm animal operation that are relevant, or more relevant, at that time can be operated upon by the monitoring system, at least because other library information might not be relevant and, as such, might not need not to be operational on premises.

Moreover, each farm animal operation can utilize farm animal operation sound types and associated information that are globally relevant to that type of farm animal operation at a particular farm animals life stage, a particular class of farm animal environments, and/or a specific location. For example, the sounds generated from a hatching operation can be specifically monitored by selection of a library of farm animal sound types from a collection of available farm animal operation sound types. Or, a hatching operation having a chick population of a particular range of chick numbers (e.g., 100-500, 500-1000, etc.) can be selected for monitoring from the farm animals sound collection of sound types. Yet further, a particular location can have sounds relevant to the operation thereof that are selectable from the library of farm animal operation sound type library. For example, the farm animal operation sound type of interest in a hatching stage may be different from that in a grow out house. In another example, a sound associated with the operation of a cooling system may be of interest in a specific farm animal operation at a specific location in the summer months, whereas that associated with a heating system may be of interest to that same location in the winter months.

Due to the fact that a collection of a specific animal type, age, etc. will likely manifest similar behavior and/or be susceptible to the same illnesses in a farm animal production setting, that is, in a first location or environment, it has been found by the inventors herein that reference farm animal operation sound data generated from a collection of one or a plurality of independent collections of farm animals that is or are evaluated by one or more trained persons to classify and label such sound data for use in machine learning processes can be used to detect, monitor, evaluate, predict, treat etc. illnesses and/or behaviors in one or more collections of farm animals having the same or similar characteristics, where such collections may comprise or be subject to one or more health condition or welfare states of interest. Therefore, in broad constructs, the present disclosure relates to methods and systems of monitoring, detecting, evaluating, predicting, treating, etc. health condition or welfare states associated with a collection of farm animals using sound data configured for use in farm animal operation monitoring events that can be useful in the automatic determination or assessment one or more farm animal condition states in a collection of the same type of farm animals desirable of detection thereof. Information derived therefrom can further be useful to generate predictions, improvements or other beneficial outcomes.

Reference farm animal collection sound data can be obtained and analyzed for the presence (or absence) of one or more condition states of interest that are associated with the farm animals or the environment(s) with which they are located. Such condition states of interest can comprise farm animal information pertinent or potentially pertinent to the health of the collection of farm animals of interest. Optionally, such health condition state information can be analyzed along with other available information such as, for example, production location operational condition states, environmental condition states proximate to the production area, or other condition states that may of interest to a farmer, farm animal operation owners or other entity, examples of which are provided hereinafter. In some aspects, reference sound data obtained from a farm animal collection of interest can be selectively analyzed using reference sound data condition information configured to detect the presence (or absence) of a selected farm animals condition state of interest.

The farm animal operation sound data obtained for evaluation as reference data can be associated with a farm animal health condition state of interest for the selected farm animal type. In this regard, reference sound data can be obtained from a farm animal collection on location, or from a plurality of locations, having one or more known or discernible health condition states where such health condition states would be desirable to detect or otherwise be of interest in another farm animal collection in a production or other setting. Such obtained reference sound data can first be collected, with any labeling or classification being first done by, or at least validated by, a human who is by a subject matter expert to ensure that the generated master machine learning libraries (i.e., the machine learning libraries from which the locally operating machine learning libraries are derived) are properly configured to provide accuracy of insights generated therefrom.

The farm animal health condition states desired to be detected or are of interest can vary according to the type of farm animals being monitored, the size and/or location of the farm animal operation in which the animals are held, as well as according to the specific lifecycle of the farm animals when the sound data is generated, among other things.

The inventors herein have determined that machine learning processes incorporating reference farm animal operation sound libraries and associated information configured to detect the presence (or absence) of poultry sounds associated with poultry illnesses can reduce the effort required to detect respiratory illness symptoms in flocks being raised in such farm animal operations. Moreover, it has been determined that the ability to accurately detect such illnesses can be improved over methods in use today. Reference farm animal operation sound data can also be generated for other lifecycle stages for poultry production, including breeder houses and hatcheries, thereby allowing production processes to be improved.

Areas where farm animals are housed inside at a farm animal operation will often be quite noisy when a collection of farm animals are active. Fans and other equipment noise present in the facility can add to the sound generated proximate to farm animal production operations that are fully or partially operated indoors or at least in constrained locations where sound can proliferate, which is a common form of farm animal operations in commercial settings. (Such enclosed operations may be desired for biosecurity reasons as appropriate for commercial farm animal production operations.) The inventors herein have found that sounds indicative of illness may not be readily discernible from a collection of farm animals during periods when high noise levels are present, for example, the daytime hours when the desire for ventilation equipment is highest, feeding and watering equipment is more frequently operational, when farm staffing is typically highest, and when the animals are awake. Accordingly, in some implementations, it can be beneficial to obtain a reference farm animal operation sound data from a collection of farm animals during a period when a substantial majority of the animals are at rest, and when there is low to no background or environmental noise. When the reference farm animal operation sound data is obtained with substantially no sound other than that emanating from the collection of farm animals themselves, such as when the animals are substantially at rest, it has been determined that a subject matter expert can more easily discern specific noises that are indicative of a health condition state of interest in those animals. For example, the reference farm animal operation sound data can be obtained when the lighting in the area where the collection of animals is substantially dark for long enough that most of the farm animals, for example chickens, are asleep or at rest, for example, by leveraging the circadian behavior of the animals.

With respect to poultry operations specifically, the amount of artificial light that is provided to chickens will vary as a function of animal age (or lifecycle stage), however, all chickens over about 3 days of age will be subjected to a lighting program with at least some darkness where the chickens can rest. Other farm animals will also sleep at regular times, and the reference farm animal operation sound data can be collected at such rest times.

As would be appreciated, chickens, as well as other vertebrates such as pigs, cattle and dairy cows are governed by a circadian rhythm that is controlled by the natural light/dark cycle of day and night. Most of their feeding and activity is during the daylight hours, and chickens and other farm animals are at rest and are generally inactive at night, especially when it is dark. At some stages of the animal production lifecycle and/or at various times of the year, farm animals can be subjected to artificial day and night, but the animals will still require some rest time where the lighting is reduced or turned off in a farm animal operation environment.

Still further, since a more optimal time to evaluate the condition of a collection of farm animals for a health condition state of interest may be when there is less movement of each animal—that is, when a large portion of the animal collection is asleep or resting—it could be difficult to achieve such rest or sleep states unless the local environment for the animals is conducive to rest or sleep. It could also be difficult to observe such rest or sleep states unless the lighting in the area of the farm animals is dimmed to an extent that good visual information is not readily obtainable from imaging devices.

In some aspects, machinery that is typically operational in proximity to the collection of animals from which reference farm animal operation sound data is being generated can optionally be shut off or deactivated when all or part of the reference farm animal operation sound data is being generated. Since the presence or absence of equipment noise can be dependent on heating or ventilation in an enclosed farm animal operation, in some implementations, it can be beneficial to acquire reference farm animal operation sound data when the external temperature of the environment where the reference farm animal operation sound data is being collected is such that heating or ventilation is less required. By excluding non-farm animal generated noise from the reference farm animal operation sound data sets, a "cleaner" or "purer" farm animals sound can be evaluated and labelled/classified by the subject matter experts, as discussed below.

In other implementations, sound equipment can be used to isolate farm animal-specific sound from sound data that includes more than just the farm animal sound, thereby providing sound data for evaluation and classification/labeling by a subject matter expert that substantially consists of sound generated from the collection of farm animals only. Such isolation can comprise part of a filtering step, and such isolated or filtered sound can be used in machine learning processes as set out further herein.

In use, microphones can be spaced at appropriate intervals within a facility in which the sound data is being collected from the collection of farm animals. Such microphone placement can be determined by one of ordinary skill in the art and, for example, can be oriented to obtain as much of the collection as practicable in a particular situation. Conventional microphones can be used, although given the often-harsh condition states in which farm animals are raised, suitably durable equipment should be selected. Microphones can be wired or wireless. Conventional digital sound collection and analysis equipment suitable for use in acquiring and processing sound data files can be used, including those specifically applicable in bioacoustics sound processing such as SoX (http://sox.sourceforge.net/), Raven (https://ravensoundsoftware.com/) as non-limiting examples thereof. One of ordinary skill in the art would be able to select appropriate sound analysis equipment and processing methodology for use in accordance with the methodologies herein.

Notifications via the audio stream and associated information processing can be directly dispatched (e.g., transmitted, sent, etc.) from the device from which the farm animal operation sound and other data are being monitored (e.g., sound processing and analysis device 105) to a user, computer, or both substantially in real time, or the notifications can be stored on the device and/or uploaded to a cloud computing server (e.g., network device 130). When a notification of the presence of a farm animal operation sound type(s) of interest and other information is automatically generated by the monitoring systems, such notification can be automatically provided to a user, supervisor, manager, or owner of the farm animal operation location, such as to a user interface. As would be appreciated, the more immediate that a notification can be, the more quickly the user, owner, supervisor, or manager can react to mitigate or prevent any damage or address any concerns that may be associated with the presence or absence of a farm animal operation sound type of interest, as well as the presence or absence of other environmental conditions of interest (e.g., heating, cooling, fan operation). It follows that such immediacy in providing the notifications can allow the farm animal operation monitoring devices of the present disclosure to more closely simulate an in-person observation or supervision of ongoing and relevant activities at the farm animal operation of interest. Alternatively, or in conjunction with the notification, the information associated with the notification can be included in onboard storage on devices operational with the farm animal operation monitoring systems, such as a user device, or separate locate separate user device. In a further implementation, each notification can be uploaded either individually—that is, as each notification occurs—or a plurality of notifications can be stored onboard the device in bulk form and then uploaded as a plurality of individual notifications to a cloud storage system.

In some implementations, a full farm animal operation audio stream and, optionally, associated information in the form of one or more of video, thermal, and/or environmental data streams, for a time period of interest can be recorded. Such time period of interest can comprise a farm animal operation monitoring event. Since the storage available on a device used to record the data acquired in each monitoring event itself may be constrained, such audio and/or other data streams can be uploaded to a cloud storage device or local server or computer as mentioned previously. The data streams can also be systematically deleted to create a full set of audio and/or video data using known methods, such as that described in U.S. Pat. No. 9,786,146, the disclosure of which is incorporated herein in its entirety by this reference.

When the farm animal operation monitoring event notifications from one or plurality of monitoring events are uploaded to a cloud storage system or a local server or computer, a plurality of notifications can be configured for presentation to in a dashboard format to provide a user, manager, supervisor, or owner of a plurality of notifications with a concise overview of a set of notifications that have occurred at the subject farm animal operation of interest or at a plurality of farm animal operation locations of interest as a collection of notifications for review. Such a dashboard configuration can allow notifications from a single farm animal operation location over a period of time or among a plurality of farm animal operations over one or more time periods to be monitored simultaneously as the notifications may be occurring substantially in real time or in a retrospective analysis.

For example, a collection of notifications generated from a farm animal operation monitoring event can be configured in a dashboard form can be collected to generate actionable information for a user, manager, supervisor, or owner of a plurality of farm animal operation locations for conditions that could be relevant to the operation thereof or associated with the quality or characteristics of the meat products generated therefrom. Still further, the collection of a plurality of notifications can provide a concise reporting configuration for one or a plurality of farm animal operations, such as to provide quality and safety tracking that can be relevant for government regulatory or legal compliance purposes, for example. The notifications can be for the presence or absence of a health or safety condition of interest, as would be appreciated. The collection of information can provide information of an incident of concern at a single farm animal operation location or at a plurality of locations.

In addition to a dashboard configuration, notifications generated in one or a plurality of farm animal monitoring event can be provided to a user on a mobile device, such as a smartphone. This feature can enhance the portability and flexibility of the farm animal operation monitoring systems, systems, and methods by allowing a user to obtain notifications as desired and, significantly, substantially when the presence or absence of a farm animal operation sound type(s) of interest is identified in the farm animal operation audio stream and any associated data.

The actions by a recipient of a farm animal operation notification that are made in response to the notifications can be recorded to further tune/improve the sound and other information libraries to subsequent use in the monitoring of a specific location or business or more generally for other monitoring processes. Human supervision can also be utilized through supervised learnings, for example, by asking the user to validate the information conveyed by a subject notification, which can facilitate generation of a ground truth for the relevant machine learning processes—such as by confirming or rejecting the correctness of information included in the sound or associated data in the relevant farm animal operation libraries that are operational on premises, as well as for inclusion in the libraries operational in the cloud computing environment. For example, if a user indicates that a farm animal operation notification is not correct or unwanted when provided, that response can be used to generate further notifications relevant to the sound type, location, farm animal operation or user.

In a further implementation, retrospective data can be collected from farm animal operation notifications collected from analysis of a plurality of farm animal operation audio streams and associated data for a single location or collection of locations, where such notifications are generated from one or a plurality of farm animal operation monitoring events. Data associated from such notifications can be used to perform modeling of the circumstances known to be associated with the subject notifications to provide predictions that might be relevant to future planning relevant to incidents that generated the subject notifications during each of the associated farm animal operation monitoring events. For example, it might be determined that certain farm animal operation sound types of interest are more likely to occur at a particular time of day, day of the week, or time of the year. In another situation, it might be determined that a farm animal operation sound type(s) of interest more often occurs when a particular farm animal operation manager is onsite. In other words, the farm animal operation notification data generated from a farm animal operation sound monitoring event can be used to develop strategies for improving operations of a specific farm animal operation location.

The various characteristics or context for each farm animal operation sound types of interest used as reference sound sources for the machine learning processes, as well as other information that can be generated from monitoring events, can be collected by a person who is on-site at a farm animal operation in which the sound type(s) of interest and other information are generated. In this regard, a person can collect one or more audio streams while on location, for example, on a mobile device having recording functionality. The collected audio stream can be labeled or tagged by the person on site, or the sound can be stored for later labelling and tagging by the person who did the collection of the audio stream, or by another person, such as a veterinarian. Once labelled and tagged, the accuracy of the audio stream characterization can be validated by either or both of a human or a computer before the subject sound type information is uploaded into a farm animal operation sound type library for use thereof. While onsite, a person can also collect environmental data, such as temperature, humidity, etc. using suitable devices. Alternatively, devices that are operational on premises can be configured to transmit real-time and/or stored data to a data capture device, such as the person's smartphone or tablet via IoT capabilities, for example. In such an implementation, the farm animal operation monitoring system can be substantially operational on location without the need for communications engagement with a cloud computing system. While the machine learning library operational on the edge computing device can be updated from time to time via downloading of sound data information from external sources, any real time operation of the livestock animal monitoring system can be operational without the need for ongoing cellular or WiFi access. Moreover, transfer of information generated from the monitoring operations can be to and from a mobile device that is itself in communications engagement with a cloud computing server. Thus, the livestock operation monitoring systems herein can be substantially operational on location where cellular coverage or internet access may be limited or even non-existent.

For example, when the reference farm animal operation animal sound data is for a chicken processing facility, the reference sound data can be analyzed for characterization of a health state of interest or other condition associated with a farm animal collection desirable for detection in a farm animal operation of interest. In another example, the welfare of cattle while prior to slaughter can be monitored. Such reference sound data can then be incorporated into a library of sound data that is operational in the monitoring systems of the present disclosure.

An insight of the inventors herein is that reference farm animal operation sound data information associated with detection or discernment of a health state of a collection of farm animals can be used in automated monitoring processes when such reference farm animal operation sound data information is generated by evaluation and classification/labeling and/or validation of at least some sound data acquired from a farm animal operation for use in the monitoring processes by one or more persons who has been trained to evaluate the health and behavior of the subject farm animals in a real life farm animal operation, that is, a subject matter expert ("SME"). However, those trained to evaluate the health condition states of farm animals in real life condition states, be they operational workers in a farm setting or clinically trained persons such as veterinarians, are not typically involved in the development of information that can suitably be used to generate information sets having appropriate characteristics desired to provide more accurate results from automated analysis of sound data generated from farm animal operations as intended herein. In fact, many of the persons who contribute to generate the necessary diagnostic information may not even have the requisite computer skills required to operate the often-sophisticated programs that serve to as the data population vehicles used to generate accurate machine learning processes.

While at least one reference set of sound data for a collection of farm animals can be acquired for use in developing sound data information suitable for use in machine learning processes, in some implementations, a plurality of generated reference farm animal operation sound data sets for a collection of farm animals can be evaluated by one or more SMEs, for labelling and tagging thereof. In this regard, 2 or 3 or 5 or 10 or more reference farm animals sound data sets can be acquired and evaluated by one or more SMEs. For example, sound data files can be acquired from a plurality of chicken grow out houses. One or more SMEs can evaluate each acquired sound data file and classify the sounds according to sound types of interest therein. To this end, sneezes or snicking can be identified, if present, in each of the sound data files, and the classified sounds can be incorporated for use in machine learning libraries associated with the sound monitoring systems and methods of the disclosure. Each of the reference farm animals sound data sets can be evaluated and classified/labeled by at least one SME having real life experience working with the subject farm animal type in a farm animal operation or appropriate operational or productions setting. Yet further, more than one SME farm animal worker can be utilized to evaluate and classify/label all or part of each obtained reference farm animal operation sound data set. An example SME farm animal worker in poultry production is the poultry flock manager. The flock manager is typically responsible for assisting in the overall success of the broiler operations for a farm operation. He will often be responsible for multiple houses/flocks at a time. The flock manager will walk through the houses on a regular schedule performing compliance checks and recording all animal and operational deviations. With appropriate experience, the flock manager develops strong insights and learnings into the animal and operational sounds in the house. These insights can enable early intervention into animal health and farm operational issues.

The generated sound data to be used as reference sound data can also be tagged for class and/or subclass can also be crowd sourced in that individuals who are present at or proximate to a farm animal operation location can be asked to record sound and include and/or validate information about sound data present in the farm animal operation sound type library that can be used in the machine learning processes that are operational according to the disclosure herein. Tagging and labeling can be gamified to incentivize participants.

Still further, a second, and perhaps more objective, review of the reference farm animal operation sound data from some or all of the collections of farm animals can optionally be generated by one or more SMEs who hold clinical training in the area of the farm animal collection desirable of detection for a health condition state of interest. For example, the reference sets of sound data can be reviewed by one or more veterinarians or other clinically trained personal for assessment of a medical diagnosis from the reference farm animal operation sound data. Academic or government researchers can also be used as SMEs. An example SME with clinical training in a poultry operation is the poultry veterinarian. The veterinarian has both formal academic training and extensive in field experience. The veterinarian is generally responsible for providing basic animal examinations, observing flock behavior, giving vaccinations, conducting inspections, evaluating meat or eggs, taking samples for analysis, making nutritional recommendations, and devising flock health management procedures. The veterinarian is trained to manage and resolve flock health risk. He or she has strong insights and learnings into the animal vocalizations enabling early interventions into animal health. Under this disclosure, the SME with clinical training would be provided tools, such as via a workflow operation mentioned previously, that can enable submission of audio data that is substantially accurately labeled or tagged with relevant health reference sound information.

Each farm animal and other sound data file generated for use in the automated farm animal operation monitoring processes for the monitoring/detection/prediction/treatment of one or more health condition or welfare states of interest of a collection of farm animals can be configurable to address a specific health state for a farm animal collection desirable of detection in each farm animal operation. In this regard, a farm animal collection thought to have a particular health condition state of interest—for example, an actual or potential disease state—can be assessed as having such a condition by a SME with experience in handling and caring for that type of farm animals comprising the collection of animals from which the reference sets of sound data are generated. Multiple health condition state information sets can be generated by correlating one or more farm animal operation sound data sets with each of an actual, real life diagnosis or health condition states generated from a collection of farm animals from which each reference farm animal operation sound data set was obtained and an associated specific health condition state or associated medical condition was obtained therefrom.

Each of the reference farm animal operation sound data sets correlated with a health condition state, etc. can operate as a filter for deriving a health condition state from a subsequently acquired sound data set that is from a collection of farm animals desirable of detection for one or more health condition states of interest. In this regard, a filter can be associated with a farm animal collection health state generated from farm animal collection sound data associated with the same farm animal collection type. As used herein, "filter" means a selection of a specific health condition state or other condition of interest associated with the farm animal collection being assessed. Thus, a "respiratory condition filter" for a flock of chickens would allow a farmer to specifically evaluate sound data for a flock of chickens to be assessed for the presence (or absence) of a respiratory condition by allowing the automatic determination of whether the sound characteristics associated with the respiratory condition was present in sound data obtained from the flock being analyzed.

As noted previously, known methods of processing the acquired sound data files can be used herein. As a general overview, the farm animal operation audio data is acquired from a farm animal operation. Sound can be recorded and saved in blocks of a certain time for example, 5, 12 or 20 seconds, where the suitable length to generate relevant information therefrom discernible without undue experimentation. In some implementations, sampling frequency can also be adapted and the optimal positioning for microphone placement in the subject environment can be determined, for example, the height of the microphone and the relative position from the walls and other sound sources that may reduce the quality of the sound type of interest (e.g. ventilation). The sound data may be processed to separate sound types into channels or to remove environmental/background sounds that are not of interest in context (e.g., fan noise, heaters). Pre-processing can comprise bandpass filtering, among other methods. When evaluating farm animal vocalizations, a method that suitably filters out background noise can be beneficial. Sufficient filtering of sound data can enhance the ability to select and classify sound events.

After preprocessing, the acquired sound data can be labelled or tagged for inclusion into the farm animal operation sound data type libraries that are used in the monitoring systems herein. As noted herein, at least some human supervision is used on at least some of the acquired farm animal operation sound data files as the libraries are being generated in the first order. Generally, however, at least some of the acquired sound data files can be automatically processed, such as by generating and assigning various metadata to each sound file, and assigning frequencies, timestamps, GPS information, etc.

After processing, feature extraction can be conducted to calculate, for example, specific audio data characteristics of the events including energy (total energy of the event, relation of the energy in different bands in the event), frequency information (peak frequency, mean frequency), spectral centroid, bandwidth, envelop of the event and zero-crossing rate. The main objective can be to identify features with physical meaning (e.g. the mean frequency of different vocalizations). The algorithm workflow generation includes the classification of the acquired farm animal operation sound types. Based on the values of the different identified features associated with the sounds, the events are assigned to different classes (e.g. chicken or turkey vocalizations into sneezes or coughs that can be further subclassified into length, quality etc.). By assigning a threshold to different features, cut-offs can be made between sound type classification. To this end, when assigning features to the acquired farm animal operation audio data, such feature assignment can be according to rules defined by an SME based on the physical meaning of a feature, such (e.g. a pig cough could never be shorter than 0.1 s or longer than 1.5 s). The features can also be assigned by someone who is not an SME, however, at least some validation of the previously classified audio files that are used in the monitoring systems of the present disclosure can be provided to ensure accuracy. Such previously assigned features can be subject to at least some SME validation for accuracy as discussed elsewhere herein. If it is determined that non-SME had high accuracy rate, that person can be subject to lighter SME supervision, in some implementations.

In a non-limiting example, the methodology for processing of bioacoustic information disclosed in Ruff et. al. ("Automated identification of avian vocalizations with deep convolutional neural networks." *Remote Sensing in Ecology and Conservation* 6, no. 1 (2020): 79-92), can suitably be used for the processing of farm animal data that is associated with chickens or turkeys and other livestock animals such as cattle, dairy cows, or pigs.

To facilitate the generation of information sets associated with reference farm animal operation sound data evaluation by SMEs, the data population process can optionally be configured in an interactive and highly user centric environment. The farm animal operation audio stream collection, labeling, and tagging functionality can be associated with an app that is configured to generate a workflow to facilitate the effort. Similarly, associated information generated from a farm animal operation monitoring event can be incorporated in a workflow application. Such labeling or tagging can be conducted fully or partially by a human supervisor either in the input stage or later in a step in which at least some of the collected sound data and, optionally, other data that may be useful, is validated for accuracy by a human supervisor. Validation of the subject sound data can be enhanced when an SME conducts the initial tagging or labeling, or the expert can perform a validation/confirmation step after the sound type is labeled for a subclass or characteristic.

For example, contemporaneously with the playing of all or a portion of a sound data file for a SME who is tasked with classifying/labeling that sound data for use in an information set, he can be presented with graphics on a screen that allow easy selection of a label for application to a specific sound data object. A selectable screen (e.g., via touch or voice) can be provided to the user along the lines of "cough, sneeze, etc." along with a selection of the intensity or duration thereof. For clinically trained SMEs a diagnosis option can be presented that can allow a more precise label to be applied. Once confirmed for accuracy, such as by validation by an SME or automated sound data analysis, such assigned data elements can be durably associated with sound data where such labeled data can be incorporated into sound data generated from subsequent collections of farm animals having health condition states desirable of detection.

The reference sound type classification, or feature generation, can be performed in an app (mobile or web based) by an authorized SME that enables easy and intuitive recording, playing and marking (labelling) of the animal sound data audio stream. This process can optionally leverage common gamification strategies. Contribution points could be assigned to an SME for each labelled data set that is submitted. Ranking and rewards could be presented to the SMEs to encourage participation in the buildout of the reference health and operational data set.

The content and identifying features of an acquired farm animal operation sound type file can be automatically analyzed against other sound data having the same or similar labelling or tagging that are already present in the sound type library prior to use of such new sound data in the library. If there is a mismatch between one or more previously uploaded sound data, the subject mismatches can be marked for SME or other human review. By "mismatch," two acquired sound data can comprise, for example, substantially identical labels or tags, but when reviewed for audio data stream characteristics, the audio streams may not be identified as comprising different sound characteristics, thus indicating that either or both of the sound files has been mis-labelled or incorrectly tagged. Either or both of a human or computer review can be provided to identify whether one or both of the sound data incorporates incorrect information. The audio file that includes incorrect information can be removed or deselected from the sound type library. In some implementations, any notifications generated using the incorrectly identified audio file can be tagged for review. Non-audio data can also be automatically or semi-automatically checked for accuracy.

Previously recorded farm animal operation sound data files (e.g., audio data 110) can also be presented to individuals for crowd sourcing of farm animal operation sound type identification prior to incorporating such sound data into the reference sound data libraries that are used in the farm animal operation monitoring processes herein. When presented for crowd sourcing, the recorded farm animal operation sound types can be tagged or labeled in the first order by a group of users. A previously tagged or labeled farm animal operation sound type recording can also be presented for validation of the labels or tags. Such information is subject to validation by an SME prior to its use in the sound data libraries used in the automated farm animal operation monitoring program.

Farm animal operation sound data that can be relevant to a location can also be collected from the specific location for use as reference sound data in subsequent monitoring operations for that or other locations. For example, one or more farm animal operation audio streams can be acquired from a location of interest or from a single location in a group of similar locations. The farm animal operation sound type(s) identified from audio files generated therefrom can be fully or partly reviewed by one or more persons with knowledge of the specific farm animal operation location or group of similar locations, that is, a SME in context. The farm animal operation audio stream data can be partially tagged or labeled prior to review by the one or more persons associated with the farm animal operation location of interest (e.g., employees, supervisors, etc.) or the one or more persons associated with the farm animal operation location can be tasked with reviewing the farm animal operation audio stream to label or tag the sound types therein for use in the sound libraries. Such labelling or tagging for a group of similar businesses or locations can be useful, for example, to maintain consistency in operations amongst a group of locations owned by a single company. When appropriately labeled/tagged, such location specific information can enrich the ability to provide context-relevant farm animal operation monitoring at least because variability as to location can be imparted to the resulting audio stream analysis. This can provide benefits over use of a globally relevant farm animal operation sound data type library that might be devoid of information that might affect the health condition or welfare states of the subject farm animal collections. For example, a sound data type that incorporates tagged and labelled sound files for a collection of turkeys at a farm animal operation in September of 3 preceding years can be compared with the sound data collected from a collection of turkeys in year 4 to determine whether there is a difference between the turkey health conditions at that location in those years in the month of September.

As would be appreciated, a farm animal operation sound library operational in conjunction with the monitoring systems of the present disclosure would benefit from being updated from time to time to include new aspects and improvements generated thereon, where such new aspects and improvements are operational in machine learning processes. Such improvements can be sourced from other farm animal operation monitoring events and information derived therefrom, where such monitoring events are running substantially autonomously in different farm animal operation locations. In this regard, more expansive farm animal operation sound libraries and sound file information can reside in a cloud computing environment, where that sound type library and associated information is configurable to collect information generated from audio stream acquisition methods that are operational in each of a plurality of locations of individual farm animal operations. The sound libraries and associated information operational in the cloud computing environment can be configured to push updated sound data and information to one or more different locations to be operational in machine learning processes operational therein on local sound acquisition and analysis devices.

In a further implementation, a plurality of sound libraries and associated information can be operational in a cloud computing environment, where such can be in communication therebetween, such as via one or more APIs configured to be operational on distributed devices at each location. Sound libraries and associated information can be moved through and among farm animal operation sound monitoring systems operational at different locations via API, as would be appreciated in the context of IoT frameworks.

The farm animal operation sound libraries and any associated information that are operational on the sound monitoring event systems of the present disclosure can be provided for purchase as a function of the class or type of sound types in marketplace or "app store" environments. For example, a farm animal operation associated with a turkey farm can purchase a sound type library for operation therein, whereas a farm animal operation associated with a free-range chicken grow operation can purchase a sound type library for that implementation. When such sound type "packages" are selected for use in a specific farm animal operation type and/or location, sound libraries and associated information appropriate for the farm animal operation of interest can be incorporated on the relevant farm animal operation sound monitoring systems to provide a "plug and play" process that can be operational substantially without sophisticated audio analysis, machine learning knowledge, or computer expertise.

Alternatively, farm animal operation sound libraries and associated information can be custom-created for a specific location or operation-type as necessary. For example, an operator of a location where there is a free-range operation that is located in a rural area may be interested in identifying the characteristic sounds of predators that may be proximate to the farm animal operation. Sound libraries associated with such fine-tuned or customized sound libraries can be pushed to the farm animal operation sound monitoring systems, also as a "plug and play" configuration. Such custom generated farm animal operation sound libraries and associated information can be incorporated into the farm animal operation sound marketplace for use by other locations or businesses.

In example implementations, the actions of the SMEs in response to review of the reference farm animal operation sound data can also be incorporated into the training sets. For example, if the SME adjusts the volume or other feature of a reference farm animal operation sound data set to more clearly discern the characteristics of that sound, information associated with the sound adjustment can be incorporated into the training set so that any time a sound having the low volume is identified, the volume adjustment can be made automatically so that the sound reaches the SME at an appropriate level. In non-limiting examples, when evaluating reference farm animal operation sound data generated from a farm animal collection that is intended for inclusion in a training set that is used in a farm animal operation monitoring process, the SME who is a farm animal operation worker, as well as an SME that is able to provide clinical diagnoses for the type of farm animals, can assess that the reference animal collection has a respiratory illness based the presence or absence of a tell-tale sign such as a cough, sneeze, chest rattle, etc., and can indicate the presence of a general respiratory illness for that collection of animals for incorporation as a feature in a training set for subsequently obtained farm animal operation sound data. In a farm animal operation, the presence of such a sound may be enough to start a medical treatment, for example using antibiotics, even while the severity of that illness to the health and safety of the flock cannot be discerned without medical assessment by a veterinarian, etc. While the SME may not be able to assess the specific type of disease state from the presence of a cough, chest rattle, sneeze, etc., the reference collection of animals may also have been medically tested in real time, that is, at the time that the reference farm animal operation sound data was generated, for the presence or absence of a specific illness. The machine learning process that utilizes these two features—that is, the presence of some respiratory illness and a separate diagnosis of the type of illness that was actually present in that collection of farm animals, can be included as a feature in machine learning processes having utility herein.

When the reference farm animal operation sound data is reviewed by both SME farm workers and, optionally, clinically trained SMEs, the results of each review can be compared and corrected against and between each other before such information is incorporated for use in machine learning processes for use in the automatic evaluation of sound data generated from collections of farm animals desirable of detection for one or more health condition or welfare states. Information about such comparisons and corrections can be implemented into machine learning operations to, for example, provide reports of the effectiveness and accuracy of each of the SMEs. Such information can also be used for training of SMEs, as well as for inclusion in the machine learning systems themselves.

Machine learning algorithms can be trained using information generated, in significant part, from incorporation of insights derivable from the SME review of the reference farm animal operation sound data generated from one or more collections of farm animals having health condition states that are known or detected. Such machine learning algorithms can be further generated from downstream applications that incorporate the evaluated and identified sound data, as well as any output data generated therefrom. For example, a training set can be used in conjunction with machine learning algorithms in assigning properties and property weights, where "weights" refers to the confidence or significance assigned to a given property associated with one or more aspects of unverified sound data generated from a collection of farm animals desirable of detection for one or more health condition states of interest.

Once one or more initial farm animal operation sound data training sets have been generated having sufficient confidence or weights of the accuracy of the results for use, new additions to the training sets can be derived from additional sound data obtained from, for example, farm animal collections having a health condition or other condition states of interest. Such data can be added by having a user, typically a SME, use light supervision to allow quick validation of the sound data to confirm correct results or throw out bad results provided by the machine learning processes. As the machine learning algorithms are further trained as to type and characteristics of the various sound data sets, the process of analyzing generated sound data can become substantially unsupervised. Even with substantially unsupervised processes monitoring processes, from time to time, a SME, optionally, can be used to validate at least some of the automatically generated farm animal health condition state determination. Over time, the machine learning algorithms can learn characteristics of one or all of the SMEs sound evaluation rules, user operations, workflow and the like with light supervision or even substantially without human supervision, and the resulting information can then be used to perform efficient and accurate farm animal collection sound data review and health condition state detection for newly provided farm animal collection sound data. Such machine learning algorithms can be updated from time to time or continuously to result in further improvements in the processes and output related thereto. As would be recognized, the machine learning predictions can be improved through continuous updates in the training in both a supervised and semi-supervised manner along with additional training for the models on the additional information. Thus, it is anticipated that, over time, inclusion of new information generated from the methodology herein will improve sound data evaluation operations, at least because improvements will be had by continuous training of the machine learning systems.

When used in the farm animal operation monitoring processes herein, the machine learning models can provide automatic review farm animal operation sound data generated from collections of farm animals having health condition states desirable of detection. Machine learning models can also be generated that allow analysis of other farm animal operation data (e.g., temperature, humidity, thermal imagery, etc.), as discussed elsewhere herein. As noted, at least some of the sound monitoring processes can be operational on premises to better ensure functionality in environments where cellular or Wi-Fi connections may be limited. In example embodiments, the collection and classification takes place at the edge (e.g., implemented in local device 105), which the machine learning processes can be done at networked devices, such as a cloud computing device, further upstream in the network from the edge device. Moreover, such local processing will also reduce latency, thus allowing notifications to be generated quickly, a fact that can improve the ability of a farm animal operation manager to act more swiftly to address health-related concerns for the subject farm animals.

Commercially available machine learning systems can be used to process the acquired sound data in a monitoring event on a local processing device including, without limitation, TensorFlow, TensorFlow Lite, IBM Data Science (i.e., Watson®), Google Machine Learning, or the like. While these, and other, commercial systems will each have proprietary variations, the basic machine learning functionalities of such systems are believed to be suitable to generate the sound data analysis processes herein and to also be appropriate for use in an edge computing or IoT operating frameworks.

In specific use cases currently contemplated by the inventors, the devices, systems, and methods of the present disclosure can enable objective, substantially real time detection of health or other conditions of interest in relation to a collection of farm animals via audio streams and, optionally, other generated data relevant to the collection, by analysis of a farm animal operation audio stream data and other data obtained from that location. By "objective," it is meant that a user, employee, supervisor, manager, or owner himself might not be required to identify and respond to a specific farm animal operation sound characteristic directly from the sound and other information. Rather, the analysis of farm animal operation sound types and other information that have been identified as potentially causing an health, welfare, safety, or operating concern to the farm animal operation can be automatically acquired, analyzed and assessed for relevance in context by a computing device operational at the location or, in some implementations, at the location and in a cloud computing environment. Thus, adherence to managerial, compliance, and safety rules can be better ensured because the human factor can be fully or partially eliminated from analysis of the occurrence of a farm animal operation sound type(s) present in a farm animal operation as occurring in a monitoring event.

The systematic and objective collection of farm animal operation sound data and associated information from each of a plurality of individual farm animal operation locations according to the devices, systems, and methods of the present disclosure can enable a number of institutional advancements related to the management of a farm animal operations. In non-limiting examples, the information generated herein can facilitate, for example: activation of an animal health or safety response more quickly as appropriate for a farm animal operation location of interest in context; provide substantially immediate notification of an animal health or safety incident of interest at a specific farm animal operation location to users or systems desiring such information; better ensure consistent and objective compliance of applicable policies and procedures at individual farm animal operation locations that are part of a collection of operations under the management or ownership of a single entity; facilitate the generation of legal documentation for an event if appropriate for a notification or record generation for one or a plurality of farm animal operations; facilitate the generation of documentation pertinent to management of humane or other certifications for one or a plurality of farm animal operations; facilitate record generation for supply chain management and accounting functions for one or a plurality of farm animal operations; activate supervisory or veterinary support for one or a plurality of farm animal operations if appropriate; and enhance and normalize training of farm animal operation personnel.

The farm animal operation manager or owner may be interested in assessing whether and how a particular parameter can affect the sounds made by a collection of farm animals during one or more lifecycle stages or over a whole lifecycle for the collection. For example, he may be interested in determining whether a supplier from whom he obtains his farm animals supply generates the consistent characteristics of farm animals at harvest than another supplier, where the characteristic can be observed from the sounds generated by the animals versus those made by animals obtained from another supplier. A supplier may generate farm animals that are less healthy at the start and, therefore, likely to be less healthy during their lifecycle (e.g., more prone to respiratory illnesses, etc.). The presence of such respiratory illnesses between different sources of animals, where the differences can be tracked back to the source of the subject livestock animals can be informative. The operator might also be interested in developing information that allows him to determine whether a particular feed source is a good choice for his farm animals; he then can run comparison sound data analyses to assess whether the health condition states are comparable during the animals' respective lifecycles. Other condition states that can be discerned from assessment of animal sounds that can be evaluated by SMEs for inclusion in sound data sets. These SMEs are people who typically possess intuitive understandings of the meaning of such sounds in context, can provide desired improvements in farm animal operations, especially in these times of fewer skilled person available to work on actual farms, as well as increased labor costs that cut into farmers profits and/or lead to increased costs to the consumer. In short, the ability to correlate farm animal operation sound data that normally is associated with skilled farm labor and, optionally, clinicians, with other features present in a farm animal operation can allow a manager to customize his farm animal operation for maximum efficiency without the extensive labor normally associated with the generation of such detailed information. Moreover, with appropriate collection of category information available for different farm animal types, even more detailed insights can be obtained by owners or operators of farm animal operations. For example, it may be possible to determine that a specific genetic line of farm animals does better when its food is supplemented one way whereas an ostensibly similar farm animals that is from a different genetic line is better suited for another feed supplement. The data generated for a collection of farm animals can therefore be used in the generation of customized feed preparations, as well as growth condition states that maximize the output obtainable by the farmer with minimal or no additional cost. As noted previously, farm animal operations are estimated to allow a operators to achieve less than 80% of the value associated with the genetic lineage of animals today. Therefore, it is anticipated that the use of properly labelled sound data information can allow the development of more accurate assessments of animal health and welfare via automated sound data monitoring. This, in turn, is expected to provide desired improvements in the growing and harvesting of farm animals for food sources.

Still further, reference farm animal operation sound data generated from other operations or condition states in a farm animal operation can be obtained for use in sound libraries that are useful in the monitoring of farm animal operations according to the disclosure herein. For example, sounds associated with the operation (or lack thereof) of automatic feeding and watering machinery can be obtained and incorporated into a training set to assess whether certain health condition states of the farm animal collections are affected by such sounds. If an automatic feeding operation results in a collection of farm animals becoming agitated, such as by waking up a flock of chickens in what was intended to be a time when sleeping is mandatory, information about whether the farm animals are experiencing unintended disruption due to operational condition states can be discerned when such information is incorporated in machine learning operations. In this regard, the generated feature can be the sound of the chickens during an expected rest period that is matched with one or more operational parameters existing in the farm animal environment at the same time.

As indicated herein, information derivable from sound data can be correlated with other information available in a farm animal operation. To this end, modern farm animal operations are highly data intensive, and many sources of data can be available for use. The methods and systems herein can allow a farm animal operation to be monitored continuously or substantially continuously for sound behavior of the subject animals resulting from either or both of the animals' health condition states or the effect of the environmental condition states thereon as such affect is manifested by the animals' sound behavior.

Yet further, reference farm animal operation sound data information generated from collections of farm animals can be used in automated monitoring events to identify health condition or welfare states resulting from unusual or unexpected condition states that may occur that have not previously been reviewed by an SME. For example, when farm animal operation sound data obtained from a collection of farm animals desirable of detection of a health condition or welfare state of interest cannot be correlated with sufficient prediction values using machine learning processes incorporating validated reference farm animal operation sound data, such sound data can be flagged for review by one or more SMEs as discussed above. Such flagged sound data can be correlated with other data obtained from the environment in which the collection of farm animals was associated so as to obtain more specific farm animal condition data for that location. In this regard, customized information pertinent to a specific farm animal operation could be generated from sound data via the monitoring methods herein. Thus, a farm animal operator may be able to improve the condition states for his farm by better understanding in context whether his animals are affected by certain operational or environmental condition states that are specific to his own operations. Moreover, automated monitoring processes incorporating such specific knowledge as features that are aligned with granular detail about the condition states of various farm animal operations can be used to improve the knowledge base for farm animal operations more generally. This is an important outcome at least because there is deep and relevant desire to improve the output of farm animal operations for the good of individual operators (e.g., farmers, owners, etc.), as well as for society in general.

An ongoing collection and analysis of sound data during all or part of the lifecycle of farm animals can assist in the generation of a "humane certification" or the like for a collection of farm animals desirable of detection of health condition state. Information about specific elements, or features, can be generated that allow a collection of farm animals, for example a flock of chickens in a grow out house, to be evaluated automatically for sounds indicative of poor health or lack of "contentedness" (such as from excess operational noise or environmental condition states causing distress) during all or part of the lifecycle of their flocks. Such sound data can be automatically reviewed for undesirable animal sound behaviors—that is, sounds that can be correlated with animal disease, discomfort, "unhappiness," "discomfort," etc.—and if no such sound behaviors were found, a certification that those farm animals lived without disease, distress etc. can be generated. Such automatic processes can reduce the amount of human labor and physical documentation collected to comply with humane certification processes.

Still further, medications, supplements etc. (e.g., prebiotics and probiotics) could be analyzed by animal demographics (farm, house, genetics, etc.), production-related data (e.g., weather, season, feed identity/amount, morbidity, diagnostics, stress, etc.), and processing data (total gain, average daily growth, cost of growth, etc.). The disclosure can provide the animal health industry new tools to test and evaluate the efficacy of these new products that can improve the overall health condition state of the farm animal collection of interest.

In a further implementation, the processes and systems herein can be used to assess the effectiveness of medical treatments generally and/or the efficacy of specific medical treatments on a collection of farm animals in need of treatment after a farm animal condition of interest is detected. In this regard, after detection of a farm animal health condition state via sound data (or by a person in real life where such information is correlated with available animal sound data), improvements (or lack thereof) in the collection of farm animals after treatment can be accessed via subsequently obtained sound data for that collection. If the subsequently obtained sound data indicates that a determined respiratory illness improves (or does not improve) after treatment, additional measures can be taken to treat the collection of farm animals. Still further, the efficacy of a treatment, for example a particular antibiotic type, can be assessed by improvement (or lack thereof) in a collection of farm animals after treatment with the specific antibiotic type. Such information can improve the knowledge base of an individual farm animals operator for his own operation over more generalized treatment parameters available today.

Further, such detailed treatment information can be incorporated into data used more broadly in farm animal operations thus improving the corpus of knowledge relating to efficient production thereof. For example, treatment effectiveness data derived from reference farm animal operation sound data generated from one or more collections of farm animals can be used to better define treatment parameters for medications, etc., given to farm animals when respiratory illnesses are identified. If fewer medications or less dosage thereof can be seen as effective treatments by close analysis of sound data obtained from farm animals after dosing where improvement is seen, not only would costs be decreased for the farmer during the lifecycle of the farm animal collection, antibiotic or other medicine use that is thought to cause detrimental effects to consumers and the environment can be reduced. Such data can be incorporated into treatment regimens and recommendations that can be deployed for use by farm animals management service providers.

The desire to eliminate proven medications (e.g., antibiotics) has moved the animal health and nutrition industry to investigate and develop new industry solutions. This disclosure provides a control system for testing these new solutions and evaluating efficacy. An example industry solution area that is being further investigated and developed is the microbiome. The microbiome in farm animals includes both animal gut health and production environment. The disclosure provides a system framework to calculate a near real-time morbidity for the farm animal collection of interest, intervene with these new industry solutions and then evaluate the farm animal collection performance.

For individual animals, periods of illness can reduce food conversion efficiency and carcass quality. Accordingly, one aspect of the present invention provides methods and systems of using sound data analysis to detect and/or predict the presence of illness in a collection of farm animals. As would be appreciated, if illness caused by one or more pathogens is not detected early, the stress of that illness may weaken one or a plurality of animals' immune systems, leaving the animal susceptible to other pathogens in the production environment which are normally resisted by a healthy animal. For example, a viral infection may increase an animal's susceptibility to infection by bacteria which are normally present in a farm animal production environment, but which are typically resisted by healthy animals. Thus, lack of timely detection and intervention for one or plurality of sick animals in a collection of farm animals can lead to use of more antibiotics and other medications that might otherwise be required with earlier detection and intervention, especially since additional pathogens may take advantage of the weakened animal. Furthermore, toxins produced by uncontrolled bacterial infections, as well as side effects of antibiotics and other medications, can damage organs and other tissues and significantly delay or prevent an animal from returning to normal food conversion efficiency and weight gain. Delays in detection of sick animals can also increase the risk of death, resulting in major economic loss. In accordance with the present disclosure, the sound data of infected farm animals provided in reference farm animal operation sound data can be compared with the sounds of a farm animal collection desirable of detection for such infection using machine learning processes to allow a user to detect the presence (or absence) of an illness in a group of farm animals wherein the group is part of the collection of farm animals.

"Cow flatulence" is known to be a major factor in methane production from agricultural operations. Such flatulence can be detected from sound data generated from one or more reference collections of dairy cows and cattle where such sound data can be evaluated by SMEs with appropriate knowledge thereof, as discussed herein. The amplitude and frequency of generated flatulence sound can be used in machine learning processes to allow improved assessment of methane emissions from cows and cattle and to analyze changes thereto as a result of modification of other condition states (feed content, etc.) that can affect the amount of flatulence that the cow or cattle generate during their lifecycles.

When the reference farm animal operation sound data is obtained at periods where most of the farm animal collection is at rest or asleep, sound from animals that are not at rest or asleep may be discernible for a collection of farm animals using the methods and systems herein. For example, animals that are ill or are experiencing some form of discomfort will be more likely to emit noises than other animals in the collection during a period of rest or sleep for the collection as a whole. As such, determination of the presence or absence of an out of scope health condition state that results in some of the animals in a farm animal collection exhibiting wakefulness sounds while the rest of the collection is exhibiting the absence of wakefulness sounds can be provided by the methods and systems herein.

Yet further, the present disclosure provides methods of automatically detecting the onset of estrus in farm animals. In farm animals that are mammals (such as beef and dairy cattle, swine, and goats), there are significant economic losses associated with missing a breeding or artificial insemination opportunity within the optimum period. Similar desires (to not miss a breeding or artificial insemination opportunity) exist with other captive mammals including horses, rare or endangered species, and utility or companion animals (pets). In most mammals and in some other animals including chickens and other birds, the onset of estrus can be accompanied by detectable changes in behavioral changes in mammals, some of which behavioral changes may be apparent in the sounds made by them. Accordingly, reference farm animal operation sound data of farm animals (or other animals) can be generated for the onset of estrus and such reference sound used in machine learning processes as discussed elsewhere herein.

In other implementations, the methods and systems herein can be used to detect the onset of labor in mammalian farm animals. Such detection using suitable reference data and machine learning processes can allow human assistance that might be used to assist such animal in delivering her offspring to be efficiently provided on an as-needed basis. For example, a farm worker or veterinarian can be automatically notified when an animal emits sounds that are indicative of the desire for birthing assistance for the animal.

In poultry hatcheries, sounds associated with various aspects of the hatching process can be automatically monitored and notifications provided as appropriate. Sound energy profiles reflecting the chick energy can be developed to provide a proxy into chick health. For example, in some hatching processes, a plurality of fertilized eggs from a source generate a collection of chicks that are not sufficiently healthy. Such sub-optimum health can be identified by acquiring sound from the hatchery for the plurality of chicks as they are pecking at the eggshells in the hatching process. A less healthy collection of chicks can be indicative of a suboptimum chicken harvest from those chicks once they reach maturity. By comparing the sound acquired from the hatching process with reference sound data that is generated from healthy hatching processes, a farm operator can generate insights into whether a collection of chicks may need to be culled at an early date. Such information can improve the overall yield of a farm operation.

Undesirable events that might negatively affect a farm animal production process can also be automatically detected using the systems and processes herein. For example, discomfort manifested in sounds emitted by a collection of farm animals may be indicative of some of the group being cold or hot or otherwise not content/comfortable. If the sounds emitted by the collection of farm animals is detected to be out of alignment with reference farm animal operation sound data that is indicative of a collection of animals that are emitting sounds indicative of pain, stress, or mistreatment, a notification can be provided that the collection of farm animals being monitored should be checked to determine whether one or more animals may need care or the treatment conditions need to be modified. As to the latter, sounds indicating stress or pain may signal that the personnel (e.g., farm workers, etc.) may be engaging in activities that are detrimental to the health or comfort of one or more farm animals in the collection. To this end, the acquisition of information that indicates that personnel may not be adhering to animal welfare policies can serve as a check even though fulltime supervision may not be provided. Such welfare monitoring via acquired sound can be substantially automatic and continuous, thus enabling an assessment of the lifecycle of a farm animal collection to be provided for a collection of farm animals, as well as individual animals in the collection.

In a further example, sounds indicative of pain or stress can automatically be acquired for livestock (e.g., cattle or pigs) can be acquired while the subject animals are being directed into a processing plant. The same holds true for chickens and turkeys that often are subjected to collection, caging, and hanging procedures that reward efficiency over animal welfare. While the meaning of "welfare" will be understood in the context of a specific farm animal or collection of farm animals, sounds associated with welfare can be related to one or more of: pain, suffering, injury, fighting, hunger, stress, among other things.

As has been increasingly recognized, hormones that are emitted by a livestock animal prior to their slaughter can influence the flavor of the meat. So, it is increasingly appreciated that it is not only more humane to reduce or eliminate the stress and pain to which farm animals are subjected to prior to slaughter, doing so can actually improve the quality/taste of the meat generated from such animals. Sounds acquired from animals from movement from the growing area (e.g., grow out house for poultry, pens for cattle) to the point of slaughter can provide information about the welfare of the animal immediately prior to slaughter.

Information about the condition of a farm animal operation can be provided to a user in real time via a dashboard or the like. Information about past operations can be generated via the dashboard or can be exported as farm animals condition reports suitable for providing to regulatory agencies and certification authorities. The machine learning processes can also be used to provide predictions of the health condition state of a farm animal collection during its current lifecycle. The reported information can include relevant features about the farm animal information, such as type of farm animals in the collection, genetic and source information, environmental condition states, operational condition states, etc. The information derivable from such reporting can also be used in machine learning processes to further improve farm animal operations. For example, if it is determined that farm animals sounds are elevated when a particular environmental event is occurring where such sound data and event correlation is provided by machine learning output information, such as a thunderstorm that causes loud agitation of a collection of farm animals, a farm animal operation can be configured to in future events to emit white noise to reduce the effect of that event on the collection of farm animals.

Figure 2:
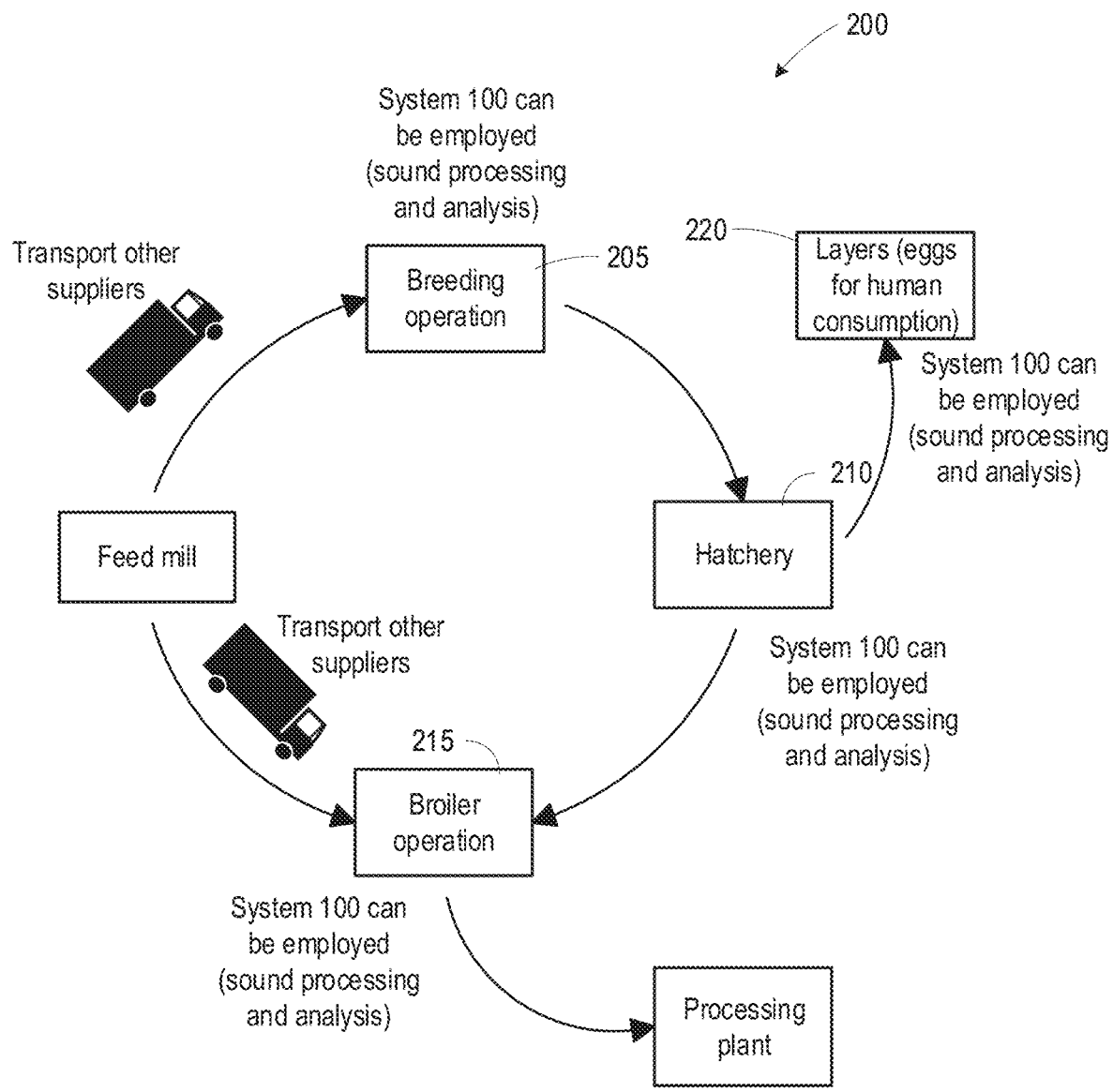
FIG. 2 is a diagram illustrating various example aspects of a poultry production process, in accordance with example embodiments of the present application.

FIG. 2 illustrates various aspects of a poultry production process 200. In various implementations, sound data, or audio analytics, can be used to generate information suitable for use in the development of processes to evaluate collections of poultry for health condition states of interest at various lifecycle stages of the animals. For example, the audio analytics systems and methods herein can be used during, for example, a breeding operation 205, hatchery 210, broiler operation 215, or an egg-laying operation 220 (e.g., laying eggs for human consumption).

Figure 3:
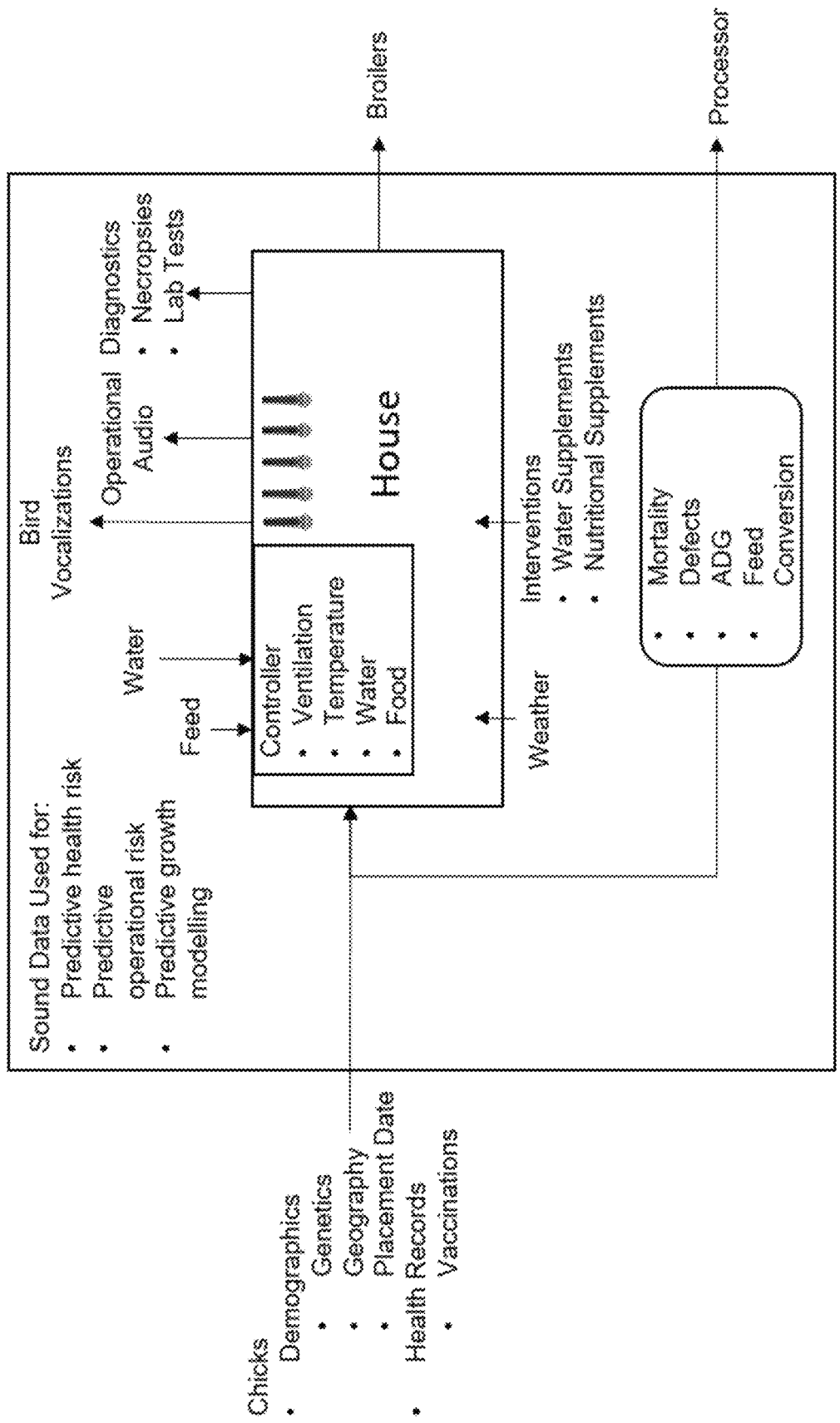
FIG. 3 is a diagram illustrating an example broiler operation control model, in accordance with example embodiments of the present application.

FIG. 3 illustrates exemplary data that can be evaluated for a poultry production process. While a poultry boiler operation control model is shown for illustrative purposes, the example data can be applicable to other control models (e.g., hatchery, breeders, etc.), and for different farm animals (e.g., pigs, cows, etc.). Examples of some data have been described above and are now described in the context of this figure, although the example data in FIG. 3 is not intended to limit the type of data that can be involved in a particular farm animal operation or environment. Example data can related to younger farm animals (e.g., younger poultry such as chicks) and can comprise demographic information, such as genetic information, geography/location identifying the origin of the chicks, placement date (e.g., placed into the operation, such as an egg-laying operation 220 or broiler operation 215, etc.) and also associated health records (e.g., vaccinations). Other example data in a poultry operation can comprise environmental data, such as ventilation data, temperature, amount of moisture, water volute, food or feed (e.g., type, quantity). In example implementations in accordance with the subject disclosure, the exemplary data can comprise sound data (e.g., derived from farm animals vocalizations, and might also include other audio generated from the location where the animals are located, such as sounds made by machinery, that may need to be filtered out, as mentioned above) that can be used for predictive health risk (e.g., identifying whether farm animals sound data are consistent with the presence or absence of a health or other condition of interest), predictive operational risk (e.g., analyzing sound data to determining whether certain operations could lead to risk of, or facilitate conditions relating to disease or other conditions of interest), and predictive growth modeling (e.g., using sound data to predict growth based on, for example, absence or presence of disease, stress, pain, etc.). Other types of data that can be collected from a farm animal operation can comprise weather information (e.g., humidity, cloud cover, outside temperature, etc.), diagnostic information (e.g., data from necropsies performed, lab test data, etc.), any interventions (e.g., water supplements, nutritional supplements, antibiotics, medicines, etc.) mortality data, data related to defects, average daily gain (ADG), feed conversion, etc.

FIG. 4 provides examples of data collection for poultry and swine production processes. The use of sound data can in example implementations be applicable to different settings and stages in an animal farm animal operation (e.g., broiler house, hatchery, nursery, etc.). Animal vocalization, as described above and below, can be used by the systems and methods herein to detect one or more health condition or welfare states of interest (e.g., respiratory disease, stress, etc.). Further, as mentioned above, other metrics or data can be analyzed to provide context, or identify the operational and environmental parameters (ventilation, temperature, etc.) in which the health condition states arise, or are correlated with.

Figure 5:
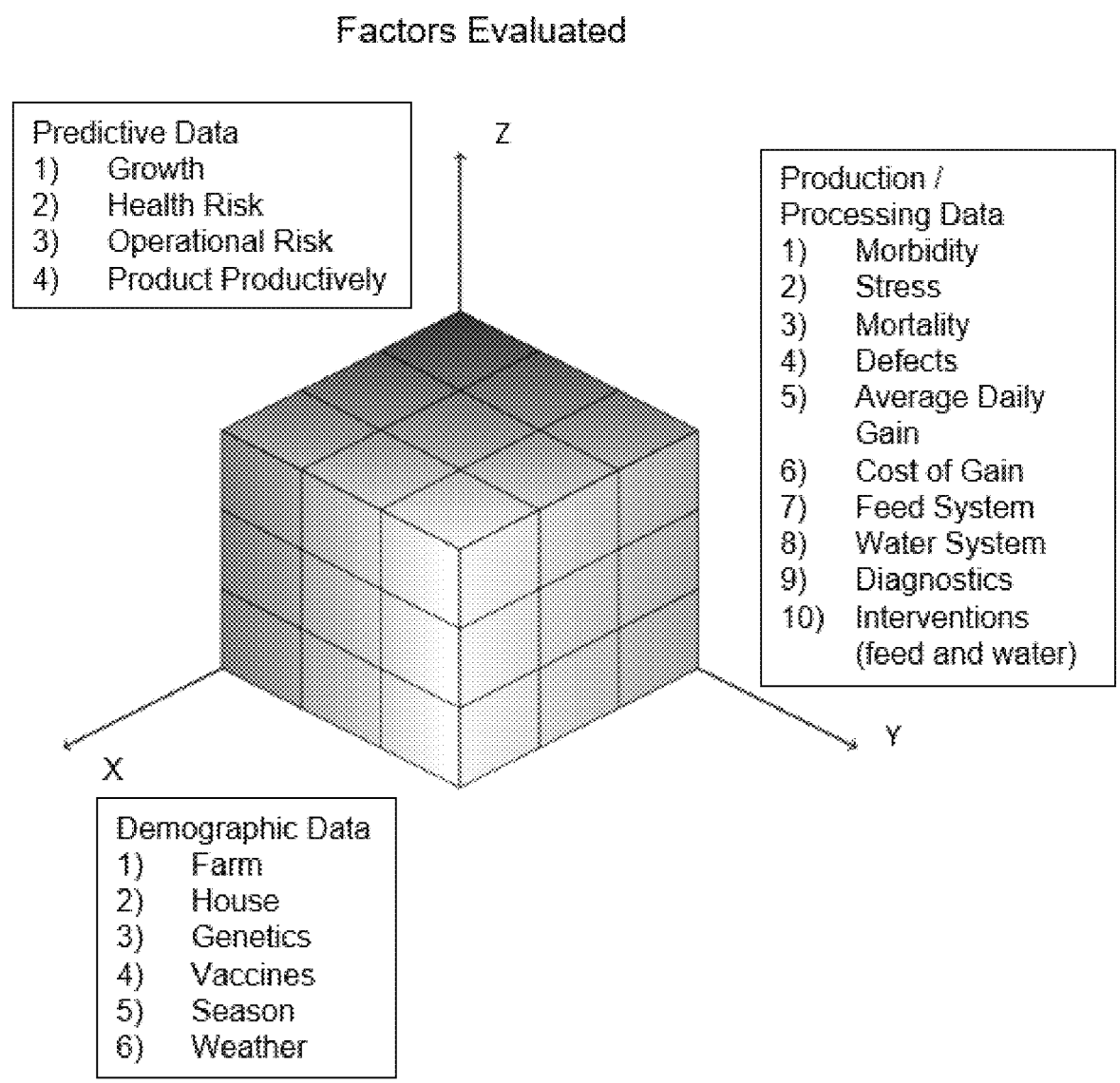
FIG. 5 illustrates example factors that can be evaluated or accounted for by system and methods in accordance with the present application.

FIG. 5 illustrates various aspects of farm animal production processes that can be evaluated to generate predictive data. For example, various animal demographic data such as the farm identity/location etc., the type of house or barn used, animal genetic features, vaccines, medicines, etc. used on the animals, weather, etc. can be captured for use to generate the information for use in machine learning processes. Such information can be used with information associated with animal production and processing data such as morbidity, stress, mortality, defects, average daily weight gain, cost of weight gain, feed system used, water system used, diagnostics, and interventions (e.g., feed and water). In example implementations, when one or more collected audio data matches reference farm animal collection sound data, one or more data elements representative of one or more of the factors (e.g., factors shown in FIG. 5 and described above) and associated with the collected audio data from a farm animal monitoring event, can be evaluated (e.g., via machine learning) to determine whether any of these factors contributed to, or are correlated with, the presence (or absence) of a health condition state of the collection of farm animals, and notifications and reports can be generated.

FIGS. 6-10 illustrate various implementations of the processes herein, including SME annotation of sound data and deployment of such sound data in machine learning (ML) processes.

Figure 6:
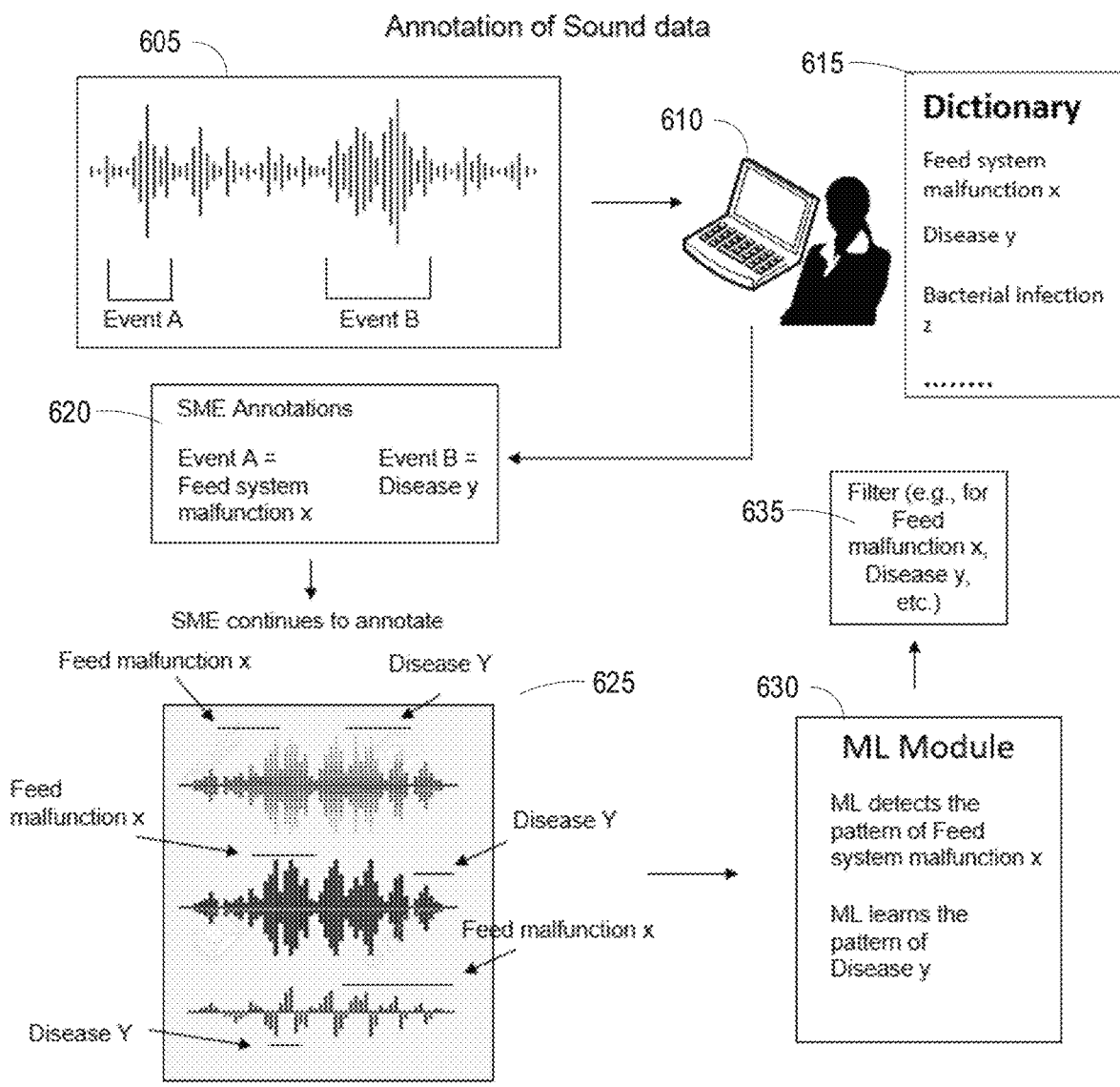
FIG. 6 depicts an example process in which sound data can be annotated, in accordance with example embodiments of the present application.

FIG. 6 shows an exemplary annotation process conducted by an SME. As shown in FIG. 6, from time to time, the SME can be prompted to check generated results and confirm that they are correct and, if not, to edit any related annotations. Reference (e.g., acquired) sound data 605 can be marked as containing abnormal (e.g., waveform associated with Event A, and waveform associated with Event B) sound types of interest by a sound data analysis module of a computing device in accordance with example implementations of the present application. The determination of whether a sound type of interest is abnormal can be determined based on, for example, comparing or distinguishing the collected sound data 605 from previously collected sound data that was determined by at least some SME analysis of reference sound data to be normal, within specification, or the like, for example. The sound data can be sent to (or accessible by) a user equipment (UE 610), such as a laptop computer, desktop computer, smartphone, tablet, etc. The UE 610 can be that associated with a SME. The sound data can be presented to the user, for example as a graph depicting a waveform, or played as an audio file (e.g., via speakers or headphones). A dictionary 615, which can be an electronic dictionary, stored in a repository in accordance with example implementations. Each SME can access the dictionary (or data bank) of possible events and identify what event A and event B are, and provide annotations 620 (e.g., the annotations serve to label or tag the respective waveforms, thus associating data elements with a sound type of interest of the sound data 605). Each item in the dictionary can have a sound data definition that corresponds to a condition state of interest (e.g., disease, feed malfunction as indicted by sounds made when farm animals are hungry, stress, etc.). The SME can, in example implementations, continue to annotate the collected sound data, resulting in further annotated sound data 625. As more sound data are collected, and annotations of for example, feed malfunction x and disease y are created, the AI engine module, or machine learning module 630, which detects patterns in the sound data, e.g., sound data related to feed malfunction x or a pattern of disease y, can create one or more filter algorithm modules 635 (e.g., for feed malfunction x or disease y). These filters can be modules that facilitate the identification of a specific event in an audio file (e.g., an audio file collected at a subsequent monitoring event of farm animals). For example, once created, the filters can identify the event, at least in some instances, when passed through a condition state filter (e.g., determining whether the collected audio data matches with a sound type of interest that is part of a reference farm animal collection sound data set).

Figure 7:
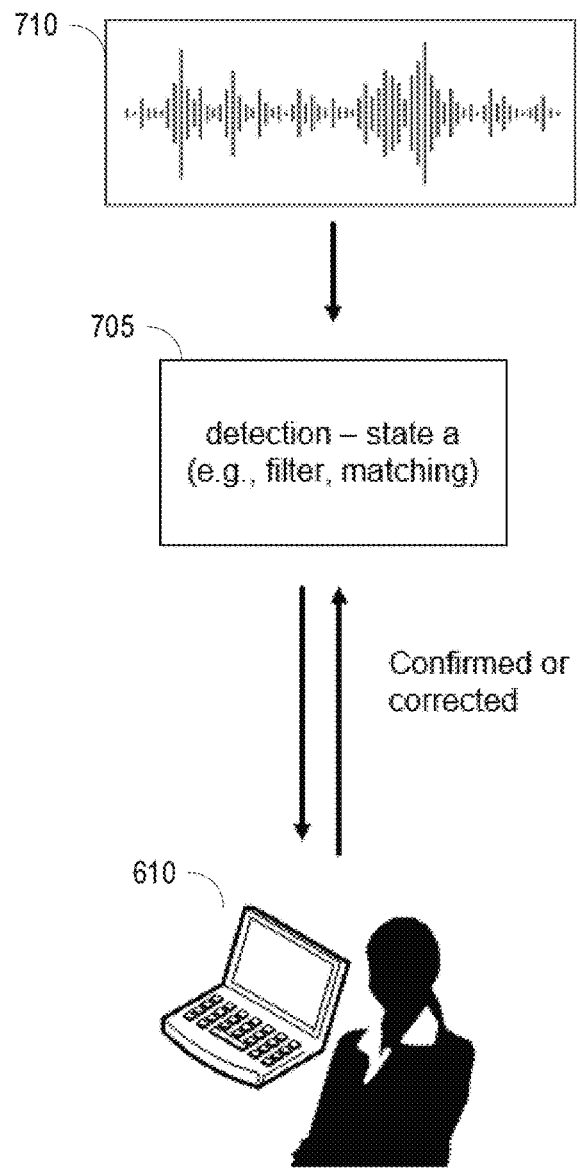
FIG. 7 shows an example process related to oversight of sound data analysis, in accordance with example embodiments of the present application.

Referring now to FIG. 7, depicting an oversight of sound data analysis model 700, in example implementations, an analysis module 705 can make a determination that one or more collected segments of audio stream data 710 from a subsequent monitoring event (distinguished for purposes of this disclosure from the audio data 605) matches the characteristics of a waveform associated with one or more waveforms of a sound type of interest in a reference farm animal collection sound database (e.g., sound type library information). If the one or more waveforms in the reference database is associated with one or more condition states of interest (e.g., sound data 605 comprising a sound type of interest that indicates for example, a feed system malfunction x, or particular disease y), a notification can be generated. The notification can be sent to, for example, a user device, e.g., SME user device 615. The notification can comprise the audio data, and can also comprise a report, which can contain additional data (e.g., operational data, environmental data, etc., as described above). The analysis module can accomplish this determination using, for example, a filter created, for example, as described in FIG. 6, based on sound data 605. The AI filter process algorithm runs and keeps a record of the audio segments that it identifies as significant (e.g., identified as a sound type of interest relating to a condition state of interest). After the determination has been made, a SME can review the audio segments the filter marks significant and correct any mistakes (e.g., marks the audio segment as a false positive), or confirm the findings of the AI filter process are correct. SME does not have to be on site (e.g., can review the audio file remotely via UE 610). This process is repeated occasionally to maintain the accuracy of the filter (or ML engine), which can be thought of as "tuning" the filter. This can be applied to each condition state filter that is generated.

Figure 8:
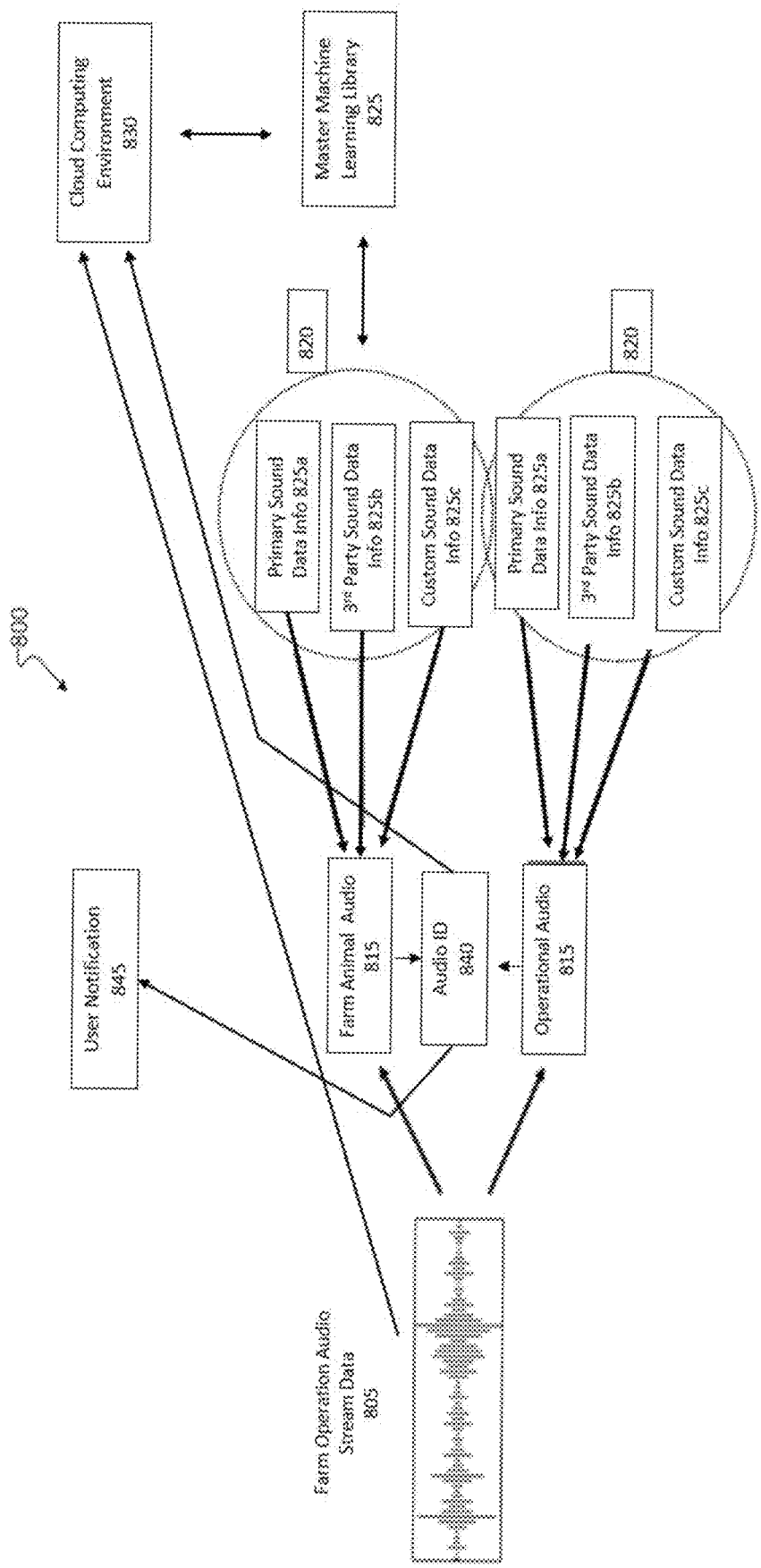
FIG. 8 illustrates an example an example environment for classification and machine learning, in accordance with example embodiments of the present application.

Non-limiting examples of various parameters of sound data analysis via filters or channels are shown in FIG. 8. Farm animal sound data monitoring system 800, which can comprise system 100, can utilize an edge computing device (e.g., local device 105), that is operational in or proximate to a farm animal operation (not shown) comprising a farm animal collection of interest (not shown) to facilitate acquisition of farm animal audio stream data 805 acquired during a farm animal sound data monitoring event. Audio stream data 805 can comprise sound data from farm animal vocalizations 810 (e.g., sounds emitted from the farm animals themselves as a collection of sounds) and farm animal operational audio stream data 815 (e.g., mechanical noise from feed systems, watering systems, HVAC, ventilation, ambient noise, weather events; etc.) System 800 is configurable to separate audio stream data 810 and 815 into source types; such as via filters or audio tracking/channels; where such separation can be in categories or classifications of farm animal origin and/or operational origin. The specific content of each of audio stream data 810 and 815 to identify the source or origin of a specific audio stream feature is provided by machine learning library 820 operational on an edge computing device (not shown) in communications engagement with system 800. Machine learning library 820. Machine learning library 820 that incorporates farm animal operation sound data from master machine learning library 825 that is operational with cloud computing environment 830.

Machine learning library 820 can incorporate sound data information generated from primary sound data 820a acquired in reference sound data acquisition events that have, for example, been at least partially reviewed by a subject matter expert prior to inclusion of such information in master machine learning library 825. As would be appreciated, the content of machine learning library 820 that is operational in system 800 can be selected from master machine learning library 825 according to various selection criteria, such as the animal collection type/size; type of animal collection of interest; health condition state of interest, etc. As mentioned, in example implementations; the while the classification can be performed at the edge (e.g., by local device 105), a cloud computing device, network device, or the such, can performed the machine learning operations as described here. It is contemplated that those of ordinary skill can, to suit a particular environment, employ implementations in which either edge or network devices to perform classification and machine learning functions.

Analysis of sound data stream 805 can also incorporate information generated from 3rd party sound data analysis information 820b. In this regard, sound data information derivable from farm animal sound data events occurring in other farm animal operations can be uploaded or otherwise made available to master machine learning library 825 for incorporation into machine learning library 820 as appropriate. In a non-limiting example, such 3rd party sound data analysis information 820b can be provided by crowd sourcing of data that is uploaded into master machine learning library 825. Such third party generated sound data analysis information 820b can be validated by a human reviewer, such as an SME, prior to being available for incorporation into machine learning library 820 from machine learning library 825.

Acquired farm animal operation sound data types 810 and 815 can also be analyzed by use of location specific sound data information 820c that is custom-generated. For example, a farm animal operator may wish to generate sound data information for the ventilation system that is operational in his specific operation. In this regard, a sound monitoring event can comprise acquisition of sound associated with the ventilation system, and such site-specific sound data information can be incorporated into machine learning library 820. When acquired farm animal operation sound data 805 includes sound having characteristics that are known to be specifically associated with the ventilation system in the subject farm operation, such sound can be identified as being from the ventilation system. Still further, the absence or reduced intensity of such ventilation sound information from acquired farm operation sound data 805 can provide information that the ventilation system was not functioning (or not functioning as expected) during a farm animal operation monitoring event. Such operational information can provide additional information to a farm animal operation manager/owner about the conditions at a location, where such conditions may have an effect on the health condition states of the farm animals located thereon.

Figure 9:
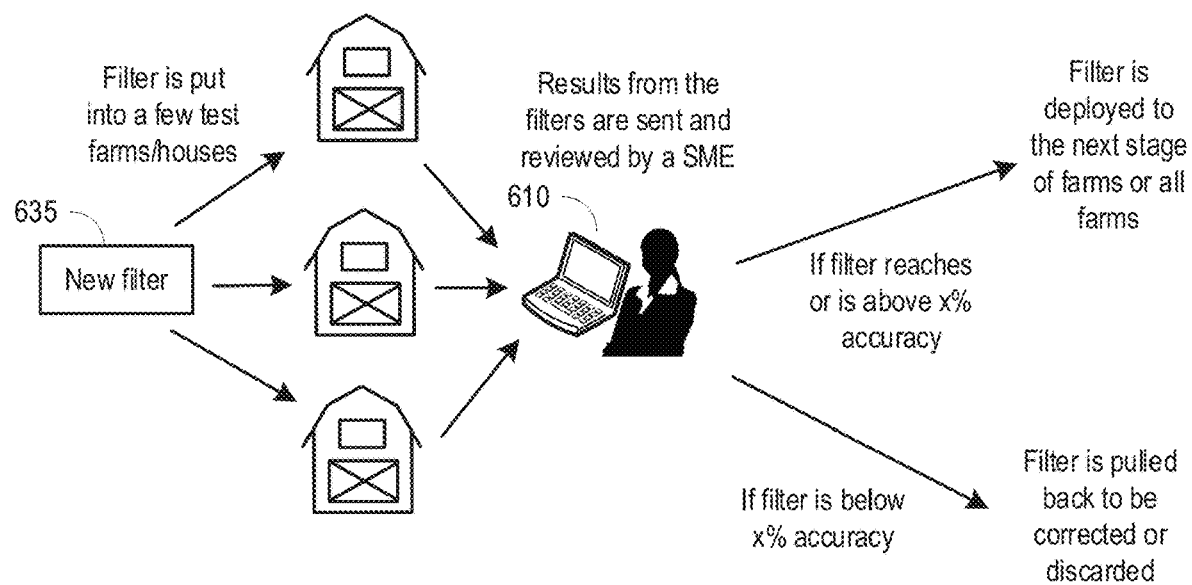
FIG. 9 illustrates an example process in which filters are sent and reviewed by a subject matter expert (SME), before wider application.

As shown in FIG. 8, farm animal operation audio identification 840 is generated. Such identification 840 can be provided to a user via notification 845 on a device, presentation on a dashboard or the like. Notification 845 can also be uploaded to cloud computing environment 830 via system 800 for use, for example, in a user dashboard format. Farm operation sound data 805 can also be uploaded into 830 for use in generating a collection of animal operation sound data for review and, in some implementations, for incorporation of information relevant thereto in master machine learning library 825 for subsequent use thereof, FIG. 9 shows an exemplary implementation where one or more health condition state filters are deployed in a limited set of locations to test the accuracy thereof. If the filter is accurate (e.g., the predicted condition state of interest matches the actual condition state of interest), the filter module can be deployed with confidence/accuracy that is above a set threshold, for example 80% or greater that the filter can correctly interpret health condition state sound data when deployed in the field. If the desired level of confidence is not obtained when the health condition state filter is deployed, the filter can be presented to one or more SMEs for recharacterization or it can be discarded.

Figure 10:
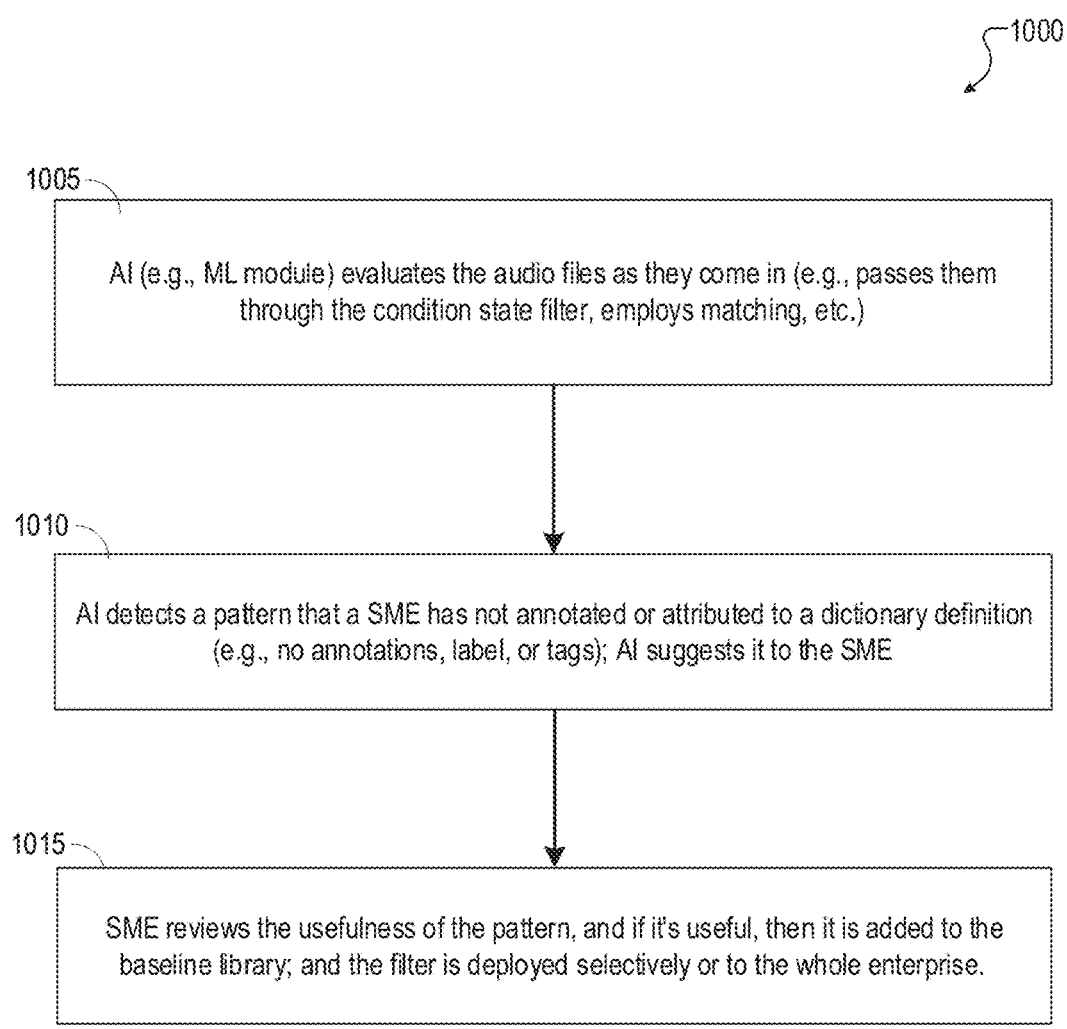
FIG. 10 illustrates a process performed by a machine learning module, in accordance with example embodiments of the present application.

FIG. 10 illustrates a further example implementation in which the ML processes is configured to evaluate animal sound data without human supervision so as to allow new health condition state sound filters to be automatically generated. Such automatically suggested filters can be presented to one or more SMEs for validation, if desired. In other words, ML module, as it digests the audio files, can recognize a new pattern that a SME has not thought of (e.g., has not annotated, or for which a SME has not provided input), A SME can review it and deem if the insight generated from the ML is useful. Referring to FIG. 10, block 1005, the AI (e.g., ML module) can evaluate the audio files as they are received and determines the applicability of reference sound data (e.g., determines a match, or passes them through the condition state filter, e.g., filter 635). The AI can detect a pattern that a SME has not attributed to a dictionary definition (e.g., no annotations, labels, or tags provided). The AI at block 1010 can make a determination, based on analysis of the data it has in its library, of a condition state of interest, and suggest it to the SME (e.g., send a message comprising a recommended label). At block 1015, the AI can detects a pattern that a SME has not been attributed to a dictionary definition, and can suggest it to the SME. The SME can review (e.g., via a user interface) the usefulness of the pattern, and if the pattern is useful, then the filter is added to the reference library (e.g., reference farm animal operation sound data). The filter can subsequently be deployed selectively to certain locations, or to the whole enterprise.

Figure 11:
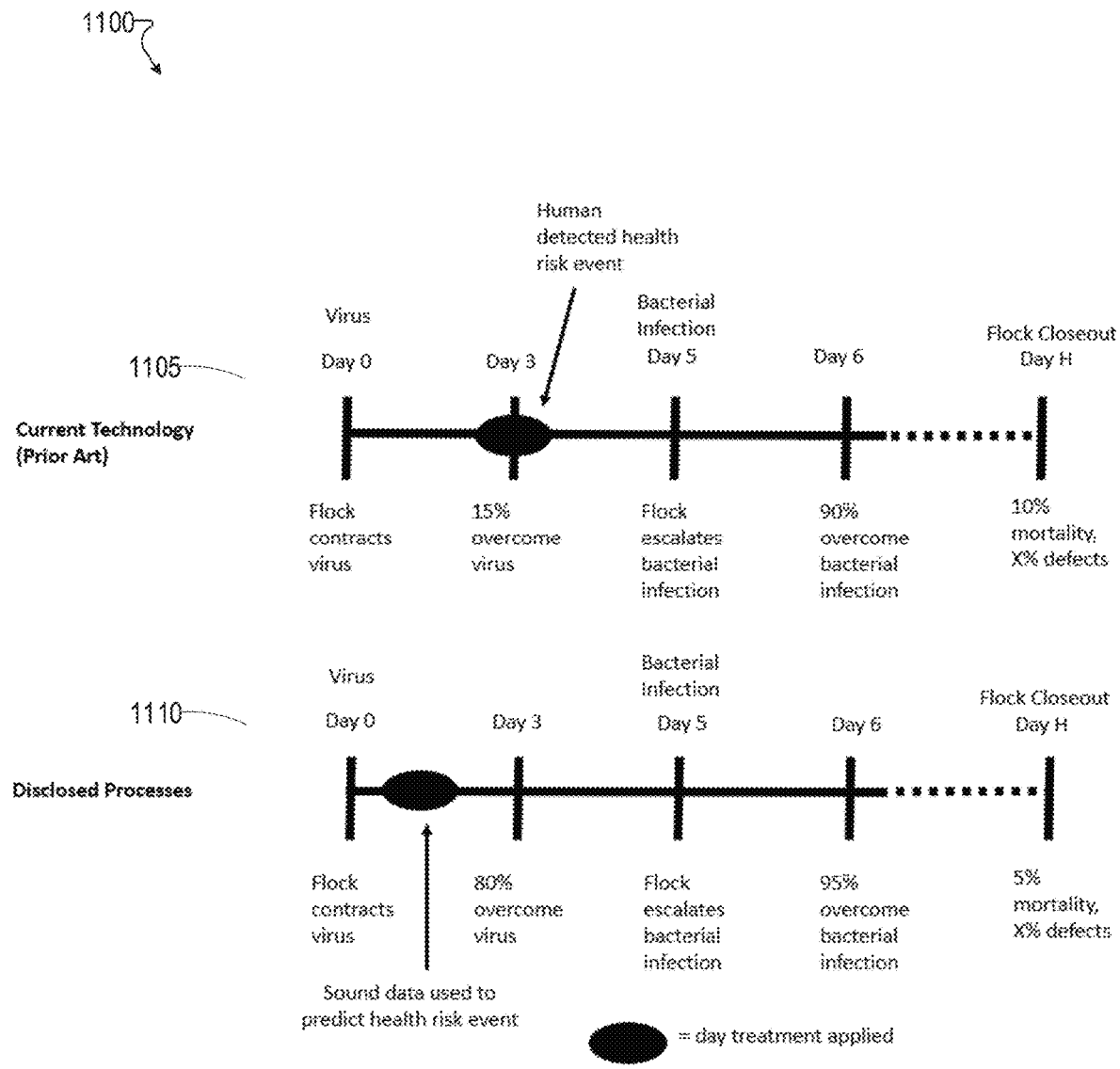
FIG. 11 illustrates the difference between detecting a condition state of interest earlier in an animal livestock operation, versus later, in accordance with example embodiments of the present application.

FIG. 11 illustrates an example in which sound data is used to detect a health condition state for a flock using the processes herein. Use of the methodology herein can allow an adverse health condition state in the flock to be detected prior to when a human is able to see such condition manifest in the flock. Application of a treatment to the flock earlier can improve the health condition state of the individual birds on a percentage basis. FIG. 11 illustrates two example timelines. The first timeline 1105 depicts a typical scenario in which the detection of a health risk event related to a collection of farm animals (e.g., poultry) is not detected until the third day of infection (e.g., in person visual inspections of flocks are typically carried out from time to time by a trained farm animals supervisor/manager). In this current scenario where intervention is delayed until a flock illness extensive enough to be observed visually, at day 3 of infection, only 15% of the flock will be healthy because 85% will have some form of virus that needs to be treated. At day 3 after treatment where the virus is detected at an earlier stage, 80% of the flock is healthy, due to the faster intervention and treatment. At day 6 of treatment, 90% of the flock will be healthy, but a portion of the flock will not be able to recover. By day H after treatment, 10% of the flock dies. On the other hand, if various implementations using sound data, or audio analytics, in accordance with the present disclosure, the survivability of a flock can be substantially improved. For example, referring to second timeline 1110, if sound data is used to predict a health risk event between day 0 and day, the overall survivability of the flock from a virus at day 6 after treatment can be improved. To this end, with early intervention enabled by health condition detection via sound data, by day 6 after treatment, 95% of the flock will be healthy, and at day H, only 5% of the flock will die. This scenario is an example only, and different diseases might have different infection and mortality rates, but the illustration is that with the use of sound data detection systems and methods that are the subject of this application, as described, mortality rates can be reduced.

Figure 12:
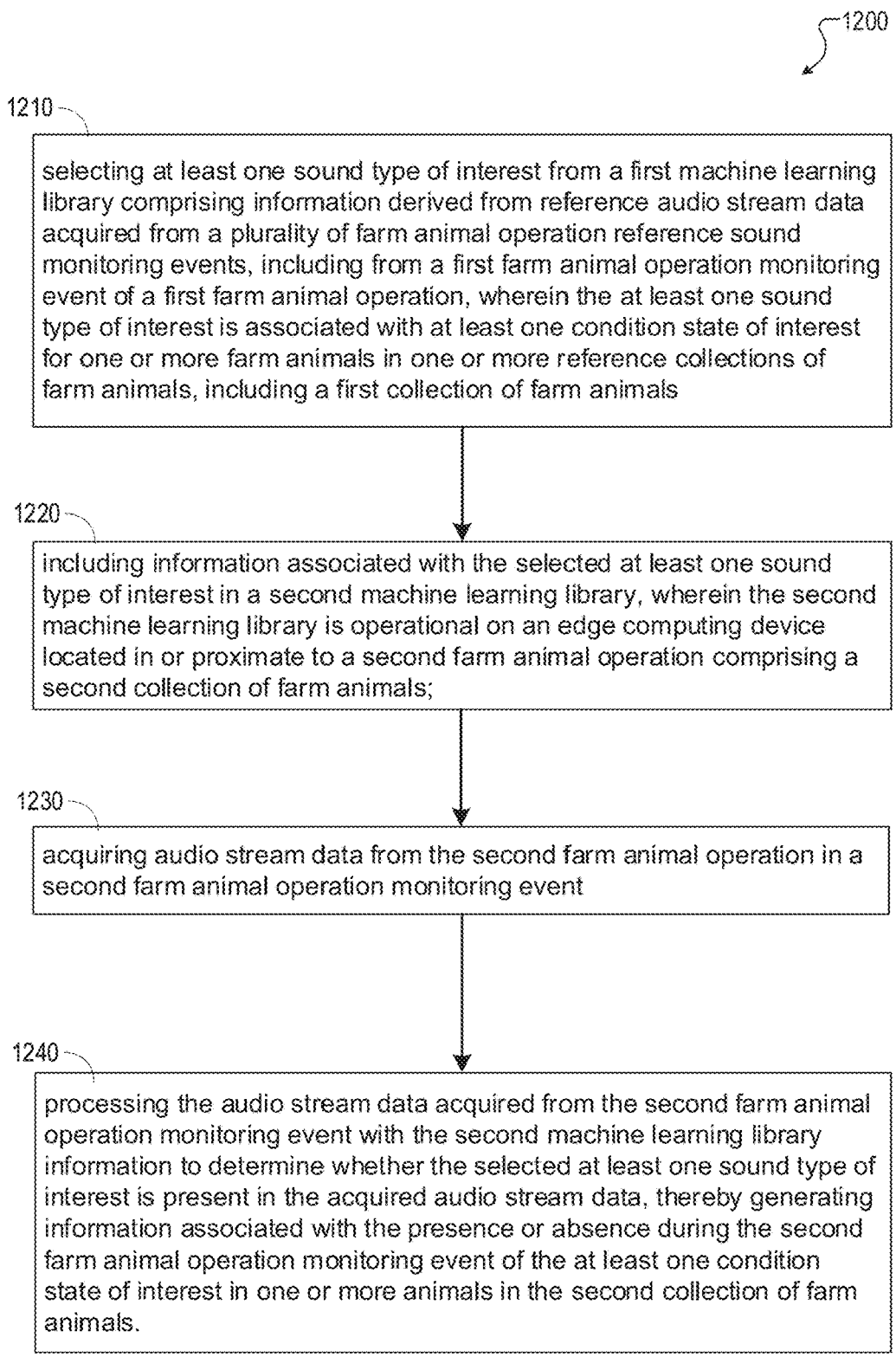
FIG. 12 depicts example operations (e.g., methods) relating to livestock monitoring that can be performed, in accordance with example embodiments of the present application.

In accordance with some example embodiments, one or more of the example methods and operations, as described above, can be performed as described in FIG. 12. The methods and operations can be performed by one or more devices (e.g., local device 105) comprising a processor and a memory. The device can have some or all of the components as described below with respect to FIG. 13. Machine-readable storage media, comprising executable instructions that, when executed by a processor, can also facilitate performance of the methods and operations described in FIG. 12. In each of these operations, steps or aspects described in one operation can be substituted or combined with steps and aspects with respect to the other operations, as well as features described, unless context warrants that such combinations or substitutions are not possible. Further, if a feature, step, or aspect is not described with respect to example operations, this does not mean that said feature, step, or aspect is incompatible or impossible with respect to those operations. As such, the example operations of the present application described above (e.g., with respect to FIGS. 1-11) and below are not necessarily limited to the steps, features, or aspects that are described with respect to those example operations. Further, steps, features, or aspects are not limited to those described in FIG. 12, and can be combined or substituted with other steps, features or aspects relating to a farm animal operation monitoring system(s) in accordance with example implementations as described in this disclosure above and below, FIG. 12 illustrates a flow diagram of example operations 1200 that can be performed, for example, by a one or more devices (e.g., local device 105, which can be an edge computing device, etc.) comprising a processor and a memory (e.g., a machine-readable storage medium) that stores executable instructions (e.g., software) that, when executed by the processor, facilitate performance of the operations described in FIG. 12. The operations described in FIG. 12 can comprise a method to monitor sounds from a farm animal operation. The edge computing device can be substantially not in communications engagement with a cloud computing server during all or part of the second farm animal operation monitoring event.

The operations 1200 can, at block 1210, comprise selecting at least one sound type of interest from a first machine learning library comprising information derived from reference audio stream data acquired from a plurality of farm animal operation reference sound monitoring events, including from a first farm animal operation monitoring event of a first farm animal operation. The at least one sound type of interest can be associated with at least one condition state of interest for one or more farm animals in one or more reference collections of farm animals, including a first collection of farm animals. At least some of the information associated with the reference audio stream data is generated by a user equipment receiving one or more inputs from a human reviewer prior to incorporation of the information into the first machine learning library. The at least one condition state of interest can relate to the health or well-being of the one or more farm animals. The condition can relate to an illness, infection, stress, feeding, etc. The first machine learning library can comprise sensor derived information derived from sensors proximate (e.g., sound collection device 115, other sensory devices 125) to the one or more farm animal operations during one or more of the plurality of farm animal operation reference sound monitoring events. At least some of the sensor derived information can be reviewed and labelled by a human reviewer prior to incorporation into the first machine learning library.

The operations 1200, at block 1220, can comprise including information associated with the selected at least one sound type of interest in a second machine learning library, wherein the second machine learning library is operational on an edge computing device located in or proximate to a second farm animal operation comprising a second collection of farm animals. The second machine learning library comprises sensor derived information generated from one or more sensors located proximate to the second farm animal operation during the second farm animal sound monitoring event. The sensor derived information can be acquired substantially concurrently with the second farm animal operation monitoring event. The sensor derived information in the second machine learning library is associated with one or more of during the second sound monitoring event: the temperature proximate to the second farm animal collection; the time of the second sound monitoring event; information associated with the operation of cooling or heating systems operational in the second farm animal collection; information associated with the operation of feeding or watering systems in the second farm animal collection; motion sensor information for areas proximate to the second farm animal collection; and weather information proximate to the second farm animal collection.

The operations 1200, at block 1230, can comprise acquiring audio stream data from the second farm animal operation in a second farm animal operation monitoring event.

The operations 1200, at block 1240, can comprise processing the audio stream data acquired from the second farm animal operation monitoring event with the second machine learning library information to determine whether the selected at least one sound type of interest is present in the acquired audio stream data, thereby generating information associated with the presence or absence during the second farm animal operation monitoring event of the at least one condition state of interest in one or more animals in the second collection of farm animals. The condition state of interest can be the presence or absence of an illness or a disease.

The operations 1200 can further comprise providing a notification to a user of whether the at least one condition state of interest is present or absent from the second collection of farm animals. The user notification can be configured for review in a dashboard generated for viewing on user equipment or in a report form.

Still referring to FIG. 12, the one or more farm animals, the first collection of farm animals, and the second collection of farm animals can comprise a collection of poultry animals, wherein the poultry animals comprise chickens or turkeys. The one or more farm animals, the first collection of farm animals, and the second collection of farm animals can comprise a collection of livestock animals, wherein the livestock animals comprise cattle, dairy cows, or pigs.

The operations 1200 can further comprise, incorporating into the first machine learning library with updated information generated from the second farm animal operation monitoring event when the edge computing device is in communications engagement with a cloud computing server. The updated information can comprise farm animal operation sound data information generated during the second farm animal operation monitoring event. The method of claim 14, wherein the farm animal operation sound data is validated by either or both of a human or a computer prior to incorporation into the first machine learning library.

A system for monitoring sounds (e.g., as described in FIG. 1, FIG. 8, FIG. 12, etc.) from a farm animal operation can comprise an edge computing device in operational engagement with at least a cloud computing server configured with a first machine library, the first machine learning library comprising information derived from a reference audio stream data acquired from a plurality of farm animal operation reference sound monitoring events, wherein the first machine learning library incorporates information associated with at least one selected farm animal condition state of interest generated from a plurality of farm animal reference sound data acquisition events. The system can also be operationally engaged with a second machine learning library, wherein the second machine learning library comprises a subset of sound data information included in the first machine library. The system can also be operationally engaged with audio stream acquisition capability in communications engagement with the edge computing device. And the system can be engaged with a power source. In the system, at least some of the farm animal operation reference sound data information in the first machine learning library is validated by a subject matter expert (SME) prior to incorporation into the subset of sound data information in the second machine learning library. The subset of sound data information can be associated with detection of the at least one selected farm animal condition state of interest. The system can be further configured to generate a notification when the at least one selected farm animal condition state of interest is detected in farm animal operation sound data acquired by the edge computing device operational in a farm animal operation monitoring event. The edge computing device can be configured to detect the at least one selected farm animal condition state of interest in farm animal operation sound data acquired by the edge computing device operational in a farm animal operation monitoring event substantially without continuous operational engagement with the cloud computing server during the monitoring event.

Figure 13:
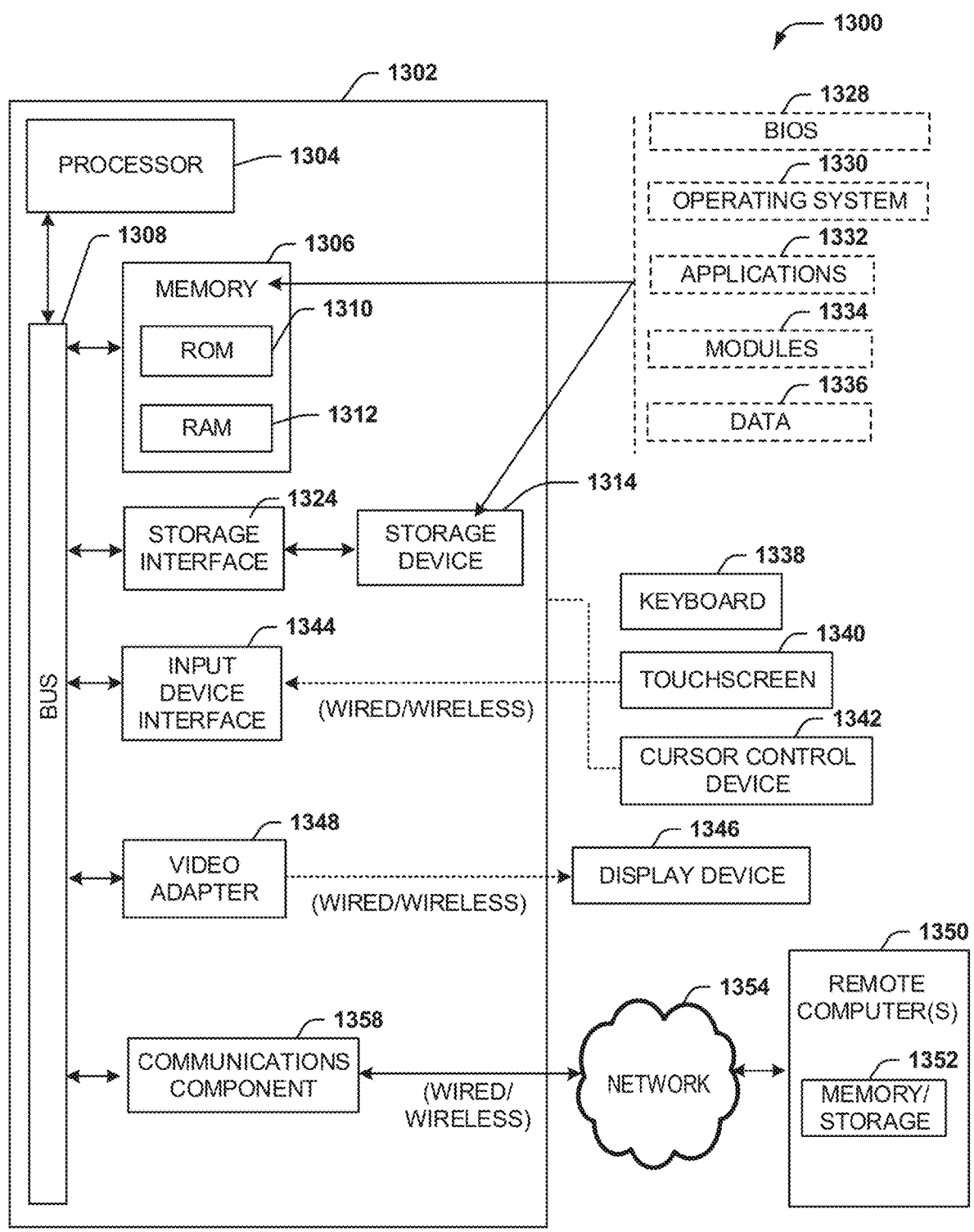
FIG. 13 depicts example devices or components that can be used to implement various aspects in accordance with example embodiments of the present application.

FIG. 13 schematically shows an example implementation of a computing system 1300. In example implementations, various devices used in the systems described above (e.g., farm animal monitoring farm animal operation monitoring system(s) 100, including farm animal sound data monitoring system 800, etc.) in accordance with this disclosure, can comprise one or more components as described in FIG. 13. The computing system 1300 can include a computer 1302 (which can be one or more computing devices, including the local device 105, network device 130, user equipment 610, sound collection device 115, other sensory devices 125, etc.). The local device 105, can be an edge computing device. Computer 1302 can comprise a processor 1304, memory 1306, various interfaces, and various adapters, each of which can be coupled via a local interface, such as system bus 1308. The system bus 1308 can be any of several types of bus structures that can interconnect to a memory bus (with or without a memory controller), a peripheral bus, and a local bus using any of a variety of commercially available bus architectures.

The processor 1304 is capable of processing computer-executable instructions that, when executed by the processor 1304, facilitate performance of operations, including methods, operations, functions, or steps described in this disclosure. The processor 1304 can comprise one of more devices that can process the instructions. The computer-executable instructions can comprise a program file, software, software module, program module, software application, etc., that is in a form that can ultimately be run by the processor 1304. The computer-executable instructions can be, for example: a compiled program that can be translated into machine code in a format that can be loaded into a random access memory 1312 of memory 1306 and run by the processor 1304; source code that may be expressed in proper format such as object code that is capable of being loaded into a random access memory 1912 and executed by the processor 1304; or source code that may be interpreted by another executable program to generate instructions in a random access memory 1312 to be executed by the processor 1304, etc. Although the software applications as described herein may be embodied in software or code executed by hardware as discussed in FIG. 13, as an alternative the same may also be embodied in dedicated hardware or a combination of software/general purpose hardware and dedicated hardware.

The computer-executable instructions can be stored on a machine-readable storage media (i.e., computer-readable storage media, also referred to as machine-readable storage medium, or as computer-readable storage medium). The computer-readable storage media can comprise memory 1306, as well as storage device 1314. The memory 1306 can represent multiple memories that operate in parallel processing circuits, and memory 1306 can comprise both nonvolatile memory (e.g., read-only memory (ROM)) and volatile memory (e.g., random access memory (RAM)), illustrated by way of example as ROM 1310 and RAM 1312.

The computer 1302 can further comprise a storage device 1314 (or additional storage devices) that can store data or software program modules. Storage device 1314 can comprise, for example, an internal hard disk drive (HDD) (e.g., EIDE, SATA), solid state drive (SSD), one or more external storage devices (e.g., a magnetic floppy disk drive (FDD), a memory stick or flash drive reader, a memory card reader, etc.), an optical disk drive 1320 (e.g., which can read or write from a compact disc (CD), a digital versatile disk (DVD), a BluRay Disc (BD), etc.). While storage device 1314 is illustrated as located within the computer 1302, the storage device 1314 can also be of the variety configured for external, or peripheral, location and use (e.g., external to the housing of the computer 1302). The storage device can be connected to the system bus 1308 by storage interface 1324, which can be an HDD interface, an external storage interface, an optical drive interface, a Universal Serial Bus (USB) interface, and any other internal or external drive interfaces.

ROM 1310, and also storage device 1314, can provide nonvolatile storage of data, data structures, databases, software program modules (e.g., computer-executable instructions), etc., which can be, for example, a basic input/output system (BIOS) 1328, an operating system 1330, one or more application programs 1332, other program modules 1334, and application program data 1336. Where any component discussed herein is implemented in the form of software, any one of a number of programming languages can be employed, such as, for example, C, C++, C#, Objective C, Java®, JavaScript®, Perl, PHP, Visual Basic®, Python®, Ruby, Flash®, or other programming languages. Data can be stored in a suitable digital format. All or portions of the operating system, applications, modules, or data can also be cached in the RAM 1312. The processor 1304 can also comprise on-chip memory to facilitate processing of the instructions. The systems and methods described herein can be implemented utilizing various commercially available operating systems or combinations of operating systems. Although the description of computer-readable storage media above refers to respective types of storage devices, it should be appreciated by those skilled in the art that other types of storage media which are readable by a computer, whether presently existing or developed in the future, could also be used in the example operating environment.

Computer 1302 can optionally comprise emulation technologies. For example, a hypervisor (not shown) or other intermediary can emulate a hardware environment for operating system 1330, and the emulated hardware can optionally be different from the hardware illustrated in FIG. 13. In such an embodiment, operating system 1330 can comprise one virtual machine (VM) of multiple VMs hosted at computer 1302.

Furthermore, operating system 1330 can provide runtime environments, such as the Java runtime environment or the .NET framework, for applications 1332. Runtime environments are consistent execution environments that allow applications 1332 to run on any operating system that includes the runtime environment. Similarly, operating system 1330 can support containers, and applications 1332 can be in the form of containers, which are lightweight, stand-alone, executable packages of software that include, e.g., code, runtime, system tools, system libraries and settings for an application.

Further, computer 1302 can be enable with a security module, such as a trusted processing module (TPM). For instance with a TPM, boot components hash next in time boot components, and wait for a match of results to secured values, before loading a next boot component. This process can take place at any layer in the code execution stack of computer 1302, e.g., applied at the application execution level or at the operating system (OS) kernel level, thereby enabling security at any level of code execution.

To the extent that certain user inputs are desirable (as indicated by the dotted line), a user can enter commands and information into the computer 1302 using one or more wired/wireless input devices, such as a keyboard 1338, a touch screen 1340, or a cursor control device 1342, such as a mouse, touchpad, or trackball. Other input devices (not shown) can comprise a microphone, an infrared (IR) remote control, a radio frequency (RF) remote control, or other remote control, a joystick, control pad, a virtual reality controller and/or virtual reality headset, a game pad, a stylus pen, an image input device (e.g., camera(s)), a gesture sensor input device, a vision movement sensor input device, an emotion or facial detection device, a biometric input device, (e.g., fingerprint or iris scanner), or the like. These and other input devices are often connected to the processing unit 1304 through an input device interface 1344 that can be coupled to the system bus 1308, but can be connected by other interfaces, such as a parallel port, an IEEE 1394 serial port, a game port, a USB port, audio port, an IR interface, a BLUETOOTH® interface, etc.

To the extent desired (as noted by the dotted line), a display device 1346, such as a monitor, television, or other type of display device, can be also connected to the system bus 1308 via an interface, such as a video adapter 1348. In addition to the display device 1346, a computer 1302 can also connect with other output devices (not shown), such as speakers, printers, etc.

The computer 1302 can operate in a networked environment using wired or wireless communications to one or more remote computers, such as a remote computer 1350 (e.g., one or more remote computers). The remote computer 1350 can be a workstation, a server computer, a router, a personal computer, a tablet, a cellular phone, a portable computer, microprocessor-based entertainment appliance, a peer device, a network node, and internet of things (IoT) device, and the like, and typically includes many or all of the elements described relative to the computer 1302, although, for purposes of brevity, only a memory/storage device 1352 is illustrated. When used in a networked environment, the computer 1302 can access cloud storage systems or other network-based storage systems in addition to, or in place of, external storage devices 1314 as described above. For example, as part of the cloud storage or network-based storage system, a remote computer 150 can comprise a computing device that is primarily used for storage, such as a network attached storage device (NAS), redundant array of disks (RADs), or a device that is a part of a SAN (storage area network), wherein the storage device comprises memory/storage 1352. In a networked environment, program modules depicted relative to the computer 1302 or portions thereof, can be stored in the remote memory/storage device 1352 (some refer to this as "cloud storage" or "storage in the cloud). Likewise, data and information, including data associated with applications or program modules, can also be stored remotely at the remote memory/storage device 1352. A remote computer 1350 that is a server device can facilitate storage and retrieval of information to a networked memory/storage device 1352. Upon connecting the computer 1302 to an associated cloud storage system, the computer 1302 can manage storage provided by the cloud storage system as it would other types of external storage. For instance, access to cloud storage sources can be provided as if those sources were stored locally on the computer 1302.

Generally, a connection between the computer 1302 and a cloud storage system can be established, either via wired or wireless connectivity, over a network 1354. The network can be, for example, wireless fidelity (Wi-Fi) network, a local area network (LAN), wireless LAN, larger networks (e.g., a wide area network (WAN)), cable-based communication network (e.g., a communication network implementing the data over cable service interface specification (DOCSIS), asynchronous transfer mode (ATM) network, digital subscriber line (DSL) network, asymmetric digital subscriber line (ADSL) network, a cellular network (e.g., 4G Long Term Evolution (LTE), 5G, etc.), and other typical fixed and mobile broadband communications networks, and can comprise components (e.g., headend equipment, local serving office equipment, Digital Subscriber Line Access Multiplexers (DSLAMs), Cable Modem Termination Systems (CMTSs), cellular nodes, etc.) related to each of these types of networks. The network 1354 can facilitate connections to a global communications network (e.g., the Internet).

When used in a networking environment, the computer 1302 can be connected to the network 1354 through a wired or wireless communications component 1358. The communications component 1358 can comprise, for example, a network work interface adapter (e.g., network interface card), wireless access point (WAP) adapter. The communications component 1358 can also comprise cellular receivers, cellular transmitters, and cellular transceivers that enable cellular communications. The communications component 1358 can facilitate wired or wireless communication to the network 1354, which can include facilitating communications through a gateway device, such as a cable modem, DSL modem, ADSL modem, cable telephony modem, wireless router, or other devices that can be used to facilitate establishment of communications. The gateway device, which can be internal or external and a wired or wireless device, can be connected to the system bus 1308 via the communications component 1358. It will be appreciated that the network connections and components shown are examples, and other methods of establishing a communications link between a remote computer 1350 can be used.

As used in this application, the terms "system," "component," "interface," and the like are generally intended to refer to a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. These components also can execute from various computer readable storage media comprising various data structures stored thereon. The components can communicate via local and/or remote processes such as in accordance with a signal comprising one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry that is operated by software or firmware application(s) executed by a processor, wherein the processor can be internal or external to the apparatus and executes at least a part of the software or firmware application. As yet another example, a component can be an apparatus that provides specific functionality through electronic components without mechanical parts, the electronic components can comprise a processor therein to execute software or firmware that confers at least in part the functionality of the electronic components. An interface can comprise input/output (I/O) components as well as associated processor, application, and/or API components.

As it is used in the subject specification, the term "processor" can refer to substantially any computing processing unit or device comprising single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, a central processing unit (CPU), an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Processors can exploit nano-scale architectures such as, but not limited to, molecular and quantum-dot based transistors, switches and gates, in order to optimize space usage or enhance performance of UE. A processor also can be implemented as a combination of computing processing units.

Furthermore, the disclosed subject matter can be implemented as a method, apparatus, or article of manufacture using standard programming and/or engineering techniques to produce software, firmware, hardware, or any combination thereof to control a computer to implement the disclosed subject matter.

The term "article of manufacture" as used herein is intended to encompass any computer-readable device, computer-readable carrier, or computer-readable storage media having stored thereon computer-executable instructions. Computing devices typically comprise a variety of media, which can comprise computer-readable storage media, which can be implemented in connection with any method or technology for storage of information such as computer-readable instructions, program modules, structured data, or unstructured data, Computer-readable storage media can be any available storage media that can be accessed by the computer, and can comprise various forms of memory, as will be elaborated further below.

In the subject specification, terms such as "store," "data store," "data storage," "database," "repository," "queue", and substantially any other information storage component relevant to operation and functionality of a component, refer to "memory components," or entities embodied in a "memory" or components comprising the memory, Memory can be of various types, such as hard-disk drives (HDD), floppy disks, zip disks, magnetic cassettes, magnetic tape, magnetic disk storage or other magnetic storage devices, flash memory devices (cards, sticks, key drives, thumb drives), cartridges, optical discs (e.g., compact discs (CD), digital versatile disk (DVD), Blu-ray Disc (BD)), a virtual device that emulates a storage device, and other tangible and/or non-transitory media which can be used to store desired information. It will be appreciated that the memory components or memory elements described herein can be removable or stationary. Moreover, memory can be internal or external to a device or component. Memory can also comprise volatile memory as well as nonvolatile memory, whereby volatile memory components are those that do not retain data values upon loss of power and nonvolatile components are those that retain data upon a loss of power.

By way of illustration, and not limitation, nonvolatile memory can comprise read only memory (ROM), programmable ROM (PROM), erasable programmable ROM (EPROM), electrically erasable programmable ROM (EEPROM), or flash memory. Volatile memory can comprise random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), magnetic random access memory (MRAM), and direct Rambus RAM (DRRAM). Additionally, the disclosed memory components of systems or methods herein are intended to comprise these and any other suitable types of memory.

The term "facilitate" as used herein is in the context of a system, device or component "facilitating" one or more actions, methods, or example operations, in respect of the nature of complex computing environments in which multiple components and/or multiple devices can be involved in some computing operations. Non-limiting examples of actions that may or may not involve multiple components and/or multiple devices comprise the methods described herein, including but not limited to transmitting or receiving data, establishing a connection between devices, determining intermediate results toward obtaining a result, etc. In this regard, a computing device or component can facilitate an operation by playing any part in accomplishing the operation (e.g., directing, controlling, enabling, etc.). When operations of a component are described herein, it is thus to be understood that where the operations are described as facilitated by the component, the operations can be optionally completed with the cooperation of one or more other computing devices or components, such as, but not limited to, processors, application specific integrated circuits (ASICs), sensors, antennae, audio and/or visual output devices, other devices, etc.

In particular and in regard to the various functions performed by the above described components, devices, circuits, systems and the like, the terms (comprising a reference to a "means") used to describe such components are intended to correspond, unless otherwise indicated, to any component which performs the specified function of the described component (e.g., a functional equivalent), even though not structurally equivalent to the disclosed structure, which performs the function in the herein illustrated example aspects of the embodiments. In this regard, it will also be recognized that the embodiments comprise a system as well as a computer-readable storage media comprising computer-executable instructions for performing the acts or events of the various methods.

Further, terms like "user equipment," "user device," "mobile device," "mobile," "station," "access terminal," "terminal," "handset," and similar terminology, can refer to a wireless device utilized by a subscriber or user of a wireless communication network or service to receive or convey data, control, voice, video, sound, gaming, or substantially any data-stream or signaling-stream. The foregoing terms are utilized interchangeably in the subject specification and related drawings. Likewise, the terms "access point," "node B," "base station," "evolved Node B," "gNodeB," "cell," "cell site," "cellular node" and the like, can be utilized interchangeably in the present application, and refer to a wireless network component or appliance that serves and receives data, control, voice, video, sound, gaming, or substantially any data-stream or signaling-stream from a set of subscriber stations. Data and signaling streams can be packetized or frame-based flows. It is noted that in the subject specification and drawings, context or explicit distinction provides differentiation with respect to access points or base stations that serve and receive data from a mobile device in an outdoor environment, and access points or base stations that operate in a confined, primarily indoor environment overlaid in an outdoor coverage area. Data and signaling streams can be packetized or frame-based flows.

Furthermore, the terms "user," "subscriber," "customer," "consumer," and the like are employed interchangeably throughout the subject specification, unless context warrants particular distinction(s) among the terms. It should be appreciated that such terms can refer to human entities, associated devices, or automated components supported through artificial intelligence (e.g., a capacity to make inference based on complex mathematical formalisms) which can provide simulated vision, sound recognition and so forth. In addition, the terms "wireless network" and "network" are used interchangeable in the present application, when context wherein the term is utilized warrants distinction for clarity purposes such distinction is made explicit.

Moreover, the word "exemplary," where used, is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion. Wherever the phrases "for example," "such as," "including" and the like are used herein, the phrase "and without limitation" is understood to follow unless explicitly stated otherwise.

As used in this application, the term "or" is intended to mean an inclusive "or" rather than an exclusive "or". That is, unless specified otherwise; or clear from context, "X employs A or B" is intended to mean any of the natural inclusive permutations. That is, if X employs A; X employs B; or X employs both A and B, then "X employs A or B" is satisfied under any of the foregoing instances.

Furthermore, references to singular components or items are intended, unless otherwise specified, to encompass two or more such components or items. For example, the articles "a" and "an" as used in this application and the appended claims should generally be construed to mean "one or more" unless specified otherwise or clear from context to be directed to a singular form.

The term "about" is meant to account for variations due to experimental error. All measurements or numbers are implicitly understood to be modified by the word about, even if the measurement or number is not explicitly modified by the word about.

The term "substantially" (or alternatively "effectively") is meant to permit deviations from the descriptive term that do not negatively impact the intended purpose. Descriptive terms are implicitly understood to be modified by the word substantially, even if the term is not explicitly modified by the word "substantially."

In addition, while a particular feature may have been disclosed with respect to only one of several implementations, such feature can be combined with one or more other features of the other implementations as may be desired and advantageous for any given or particular application. To the extent that the terms "has," "have", "having", "comprising" and "including" and "involving" and variants thereof (e.g., "comprises," "includes," and "involves") are used interchangeably and mean the same thing—these terms are defined consistent with the common patent law definition of "comprising" and is therefore interpreted to be an open term meaning "at least the following but is not limited to," and as such is not to be interpreted to exclude additional features, limitations, aspects, etc.

The above descriptions of various example embodiments and example implementations of the subject disclosure, corresponding figures, and what is described in the Abstract, are described herein for illustrative purposes, and are not intended to be exhaustive or to limit the disclosed embodiments to the precise forms disclosed. It is to be understood that one of ordinary skill in the art can recognize that other embodiments comprising modifications, permutations, combinations, and additions can be implemented for performing the same, similar, alternative, or substitute functions of the disclosed subject matter, and are therefore considered within the scope of this disclosure.

For example, disclosed systems and apparatuses and components or subsets thereof (referred to hereinafter as components) should neither be presumed to be exclusive of other disclosed systems and apparatuses, nor should an apparatus be presumed to be exclusive to its depicted components in an example embodiment or embodiments of this disclosure, unless where clear from context to the contrary. Additionally, steps or blocks as shown in example methods, or operations, can be interchangeable with steps or blocks as show in other example methods or operations. The scope of the disclosure is generally intended to encompass modifications of depicted embodiments with additions from other depicted embodiments, where suitable, interoperability among or between depicted embodiments, where suitable, as well as addition of a component(s) from one embodiment(s) within another or subtraction of a component(s) from any depicted embodiment, where suitable, aggregation of components (or embodiments) into a single component achieving aggregate functionality, where suitable, or distribution of functionality of a single system or component into multiple systems or components, where suitable. In addition, incorporation, combination or modification of systems or components depicted herein or modified as stated above with systems, apparatuses, components or subsets thereof not explicitly depicted herein but known in the art or made evident to one with ordinary skill in the art through the context disclosed herein are also considered within the scope of the present disclosure. As such, although a particular feature of the present invention may have been illustrated or described with respect to only one of several implementations, any such feature may be combined with one or more other features of the other implementations as may be desired and advantageous for any given or particular application.

Therefore, the disclosed subject matter should not be limited to any single embodiment described herein, but rather should be construed in breadth and scope in accordance with the claims, including all equivalents, that are listed below.

What is claimed is:

1. A method to monitor one or more condition states of interest associated with a farm animal operation comprising:
   a) receiving, by a computer, first farm animal operation sound information in a first farm animal operation sound monitoring event of a first farm animal operation identified for monitoring for a presence or absence of the one or more condition states of interest, wherein the first farm animal operation comprises a collection of farm animals;
   b) comparing, by the computer, the received first farm animal operation sound information with one or more selected farm animal operation reference sound types selected from a machine learning library comprising a collection of farm animal operation information wherein:
   i) the collection of farm animal operation information comprises a plurality of farm animal operation reference sound types generated from one or more farm animal operations in a plurality of prior farm animal operation sound collection events associated with the one or more farm animal operations;
   ii) each selected farm animal operation reference sound type is associated with a presence or absence of a specific farm animal operation condition state of interest; and
   iii) prior to incorporation in the collection of farm animal operation information, each farm animal operation reference sound type has been validated by a human reviewer as being associated with the presence or absence of each specific farm animal operation condition state of interest;
   c) detecting, by the computer, whether at least one of the one or more selected farm animal operation reference sound types is present in the received first farm animal operation sound information; and
   d) generating, by the computer, information about a presence or absence of each specific farm animal operation condition state of interest in the first farm animal operation during the first farm animal operation sound monitoring event.

2. The method of claim 1, further comprising providing, by the computer, a notification to the user of whether the farm animal operation condition state of interest is present or absent in the first farm animal operation.

3. The method of claim 2, wherein the user notification is configured for review in a dashboard generated for viewing on user equipment or in a report format.

4. The method of claim 1, wherein one or more farm animal operation condition states of interest are associated with one or more farm animals in the collection of farm animals in the first farm animal operation.

5. The method of claim 1, wherein one or more farm animal operation condition states of interest are associated with one or more of:
   a) a temperature proximate to the collection of farm animals;
   b) an activity level of one or more animals in the collection of farm animals;
   c) operational information for heating or cooling systems associated with areas proximate to the collection of farm animals;
   d) operational information for feeding or watering systems associated with the collection of farm animals; and
   e) weather information proximate to a farm animal collection during a prior farm animal operation sound collection event.

6. The method of claim 1 operational on an edge computing device that is substantially not in communications engagement with a cloud computing device during all or part of the first farm animal operation sound monitoring event.

7. The method of claim 6, wherein information from the first farm animal operation sound monitoring event is provided to the cloud computing device when the edge computing device is in communications engagement with the cloud computing device.

8. The method of claim 1, wherein the plurality of prior farm animal operation sound collection events is associated with the first farm animal operation and the method further comprises generating information about one or more operational differences in the first farm animal operation detected from information derived from the plurality of prior farm animal operation sound collection events.

9. The method of claim 1, wherein the plurality of prior farm animal operation sound collection events are associated with farm animal operations that are different from the first farm animal operation and the method further comprises generating information about one or more operational differences in the first farm animal operation detected from information derived from the plurality of prior farm animal operation sound collection events not associated with the first farm animal operation.

10. The method of claim 1, wherein the collection of farm animals comprises poultry animals.

11. The method of claim 1, wherein the collection of farm animals comprises cattle, dairy cows, or pigs.

12. The method of claim 1, wherein the farm animal operation condition state of interest is associated with a farm animal illness or a disease.

13. The method of claim 1, wherein the farm animal operation condition state of interest is associated with a farm animal welfare state.

14. The method of claim 1, wherein:
 a) the machine learning library further comprises information derived from sensors located proximate to each of the one or more farm animal operations during each of the plurality of prior farm animal operation sound collection events; and
 b) at least some of the sensor derived information is reviewed and labelled by the human reviewer prior to incorporation into the collection of farm animal operation information.

15. A system for monitoring sounds generated from a farm animal operation during a farm animal operation sound monitoring event comprising:
 a) an edge computing device in operational engagement with at least:
  i) a cloud computing server configured with a first machine learning library, the first machine learning library comprising a collection of farm animal operation reference sound data information derived from reference audio stream data acquired from a plurality of farm animal operation reference sound monitoring events, wherein the collection of farm animal operation reference sound data information incorporates information associated with one or more selected farm animal operation condition states;
  ii) a second machine learning library, wherein the second machine learning library comprises a selected subset of farm animal operation reference sound data information associated with a presence or absence of one or more farm animal operation condition states of interest;
  iii) audio stream acquisition capability in communications engagement with the edge computing device; and
  iv) a power source;
 where the edge computing device is configured to:
 a) receive first farm animal operation sound information in a first farm animal operation sound monitoring event of a first farm animal operation identified for monitoring for a presence or absence of the one or more condition states of interest, wherein the first farm animal operation comprises a collection of farm animals;
 b) compare the received first farm animal operation sound information with one or more selected farm animal operation reference sound types selected from the first machine learning library comprising a collection of farm animal operation information wherein:
  i) the collection of farm animal operation information comprises a plurality of farm animal operation reference sound types generated from one or more farm animal operations in a plurality of prior farm animal operation sound collection events associated with the one or more farm animal operations;
  ii) each selected farm animal operation reference sound type is associated with a presence or absence of a specific farm animal operation condition state of interest; and
  iii) prior to incorporation in the collection of farm animal operation information, each farm animal operation reference sound type has been validated by a human reviewer as being associated with the presence or absence of each specific farm animal operation condition state of interest;
 c) detect whether at least one of the one or more selected farm animal operation reference sound types is present in the received first farm animal operation sound information; and
 d) generate information about a presence or absence of each specific farm animal operation condition state of interest in the first farm animal operation during the first farm animal operation sound monitoring event.

16. The system of claim 15, wherein at least some of the collection of farm animal operation reference sound data information in the first machine learning library is validated by a human reviewer prior to incorporation into the selected subset of farm animal operation reference sound data information in the second machine learning library.

17. The system of claim 15, wherein the selected subset of farm animal operation reference sound data information is associated with detection of the presence or absence of the one or more farm animal operation condition states of interest.

18. The system of claim 17, further configured to generate a notification when the presence or absence of the one or more farm animal operation condition states of interest is detected in farm animal operation sound data acquired by the edge computing device operational in the farm animal operation sound monitoring event.

19. The system of claim 15, wherein the edge computing device is configured to detect a presence or absence of the one or more farm animal operation condition states of interest in farm animal operation sound data acquired by the edge computing device operational in a farm animal operation monitoring event substantially without continuous operational engagement with the cloud computing server during the farm animal operation sound monitoring event.

20. The system of claim 15, further comprising at least one sensor in operational engagement with the edge computing device, wherein the at least one sensor is configured to acquire information associated with a farm animal operation during the farm animal operation sound monitoring event.

* * * * *